US012065673B2

(12) United States Patent
Deschaseaux et al.

(10) Patent No.: US 12,065,673 B2
(45) Date of Patent: Aug. 20, 2024

(54) METHOD FOR OBTAINING HUMAN BROWN/BEIGE ADIPOCYTES

(71) Applicants: ETABLISSEMENT FRANCAIS DU SANG, La Plaine Saint Denis (FR); INSTITUT NATIONAL DE LA SANTE ET DE LA RECHERCHE MEDICALE, Paris (FR); UNIVERSITE TOULOUSE III—PAUL SABATIER, Toulouse (FR); CENTRE NATIONAL DE LA RECHERCHE SCIENTIFIQUE, Paris (FR)

(72) Inventors: Frederic Deschaseaux, Toulouse (FR); Fabien Guilloton, Toulouse (FR); Sandra Muller, Toulouse (FR); Luc Sensebe, Joue les Tours (FR); Louis Casteilla, Toulouse (FR); Audrey Carriere-Pazat, Lacroix-Falgarde (FR)

(73) Assignees: ETABLISSEMENT FRANCAIS DU SANG, La Plaine Saint Denis (FR); INSTITUT NATIONAL DE LA SANTE ET DE LA RECHERCHE MEDICALE, Paris (FR); UNIVERSITE TOULOUSE III—PAUL SABATIER, Toulouse (FR); CENTRE NATIONAL DE LA RECHERCHE SECIENTIFIQUE, Paris (FR)

( * ) Notice: Subject to any disclaimer, the term of this patent is extended or adjusted under 35 U.S.C. 154(b) by 605 days.

(21) Appl. No.: 15/743,062

(22) PCT Filed: Jul. 8, 2016

(86) PCT No.: PCT/EP2016/066361
§ 371 (c)(1),
(2) Date: Jan. 9, 2018

(87) PCT Pub. No.: WO2017/009263
PCT Pub. Date: Jan. 19, 2017

(65) Prior Publication Data
US 2018/0216070 A1 Aug. 2, 2018

(30) Foreign Application Priority Data

Jul. 10, 2015 (EP) .................................... 15306153

(51) Int. Cl.
*C12N 5/077* (2010.01)
*A61K 35/35* (2015.01)
*C12N 5/0775* (2010.01)
*G01N 33/50* (2006.01)

(52) U.S. Cl.
CPC ............ *C12N 5/0653* (2013.01); *A61K 35/35* (2013.01); *C12N 5/0663* (2013.01); *C12N 5/0667* (2013.01); *G01N 33/50* (2013.01); *G01N 33/5044* (2013.01); *C12N 2501/105* (2013.01); *C12N 2501/11* (2013.01); *C12N 2501/115* (2013.01); *C12N 2501/155* (2013.01); *C12N 2501/165* (2013.01); *C12N 2501/33* (2013.01); *C12N 2501/999* (2013.01); *C12N 2502/115* (2013.01); *C12N 2506/13* (2013.01); *C12N 2506/1346* (2013.01); *C12N 2513/00* (2013.01)

(58) Field of Classification Search
CPC .............................. A61K 35/35; C12N 5/0653
See application file for complete search history.

(56) References Cited

U.S. PATENT DOCUMENTS

| | | | | |
|---|---|---|---|---|
| 2006/0110825 | A1* | 5/2006 | Alessandri | C12N 5/0667 435/368 |
| 2013/0209418 | A1* | 8/2013 | Seyda | A61K 35/35 424/93.7 |
| 2014/0140967 | A1* | 5/2014 | Saeki | A61K 35/28 424/93.7 |
| 2015/0202234 | A1* | 7/2015 | Gillette | A61K 35/35 424/93.7 |

FOREIGN PATENT DOCUMENTS

| | | | | |
|---|---|---|---|---|
| EP | 2692868 A1 * | 2/2014 | ..... | C12Y 207/01002 |
| WO | WO-2014026201 A1 * | 2/2014 | ..... | C12N 5/0653 |

OTHER PUBLICATIONS

Wang et al., "3D spheroid culture system on micropatterned substrates for improved differentiation efficiency of multipotent mesenchymal stem cells", Biomaterials, vol. 30, (2009) pp. 2705-2715. (Year: 2009).*
Huang et al., "BMP signaling pathway is required for commitment of C3H10T1/2 pluripotent stem cells to the adipocyte lineage", PNAS, 2009, vol. 106, No. 31, pp. 12670-12675. (Year: 2009).*
Huttala, O. et al. "Human Vascular Model with Defined Stimulation Medium—A Characterization Study" *ALTEX*, 2015, pp. 125-136, vol. 32, No. 2.
Carrière, A. et al. "Browning of White Adipose Cells by Intermediate Metabolites: An Adaptive Mechanism to Alleviate Redox Pressure" *Diabetes,* Oct. 2014, pp. 3253-3265, vol. 63, No. 10.
Lin, R-Z. et al. "Human white adipose tissue vasculature contains endothelial colony-forming cells with robust in vivo vasculogenic potential" *Angiogenesis,* Oct. 2013, pp. 1-14, vol. 16, No. 4.
Lo, K. A. et al. "Turning WAT into BAT: a review on regulators controlling the browning of white adipocytes" *Bioscience Reports,* Jul. 30, 2013, pp. 711-719, vol. 33.
Ning, H. et al. "Effects of EdU Labeling on Mesenchymal Stem Cells" *Cytotherapy,* Jan. 1, 2013, pp. 1-13, vol. 15, No. 1.

(Continued)

*Primary Examiner* — Laura Schuberg
(74) *Attorney, Agent, or Firm* — SALIWANCHIK, LLOYD & EISENSCHENK

(57) ABSTRACT

The present invention concerns a method of producing brown/beige adipocytes from white adipose tissue cells and/or mesenchymal stem cells, in particular from subcutaneous white adipose tissue cells, and the use of said brown/beige adipocytes in a cell based therapy of a subject or in screening platforms.

20 Claims, 13 Drawing Sheets

(56) References Cited

OTHER PUBLICATIONS

Okla, M. et al. "BMP7 Drives Human Adipogenic Stem Cells into Metabolically Active Beige Adipocytes" *Lipids,* 2015, pp. 111-120, vol. 50, No. 2.
Park, A. et al. "Distinction of white, beige and brown adipocytes derived from mesenchymal stem cells" *World Journal of Stem Cells,* Jan. 26, 2014, pp. 33-42, vol. 6, No. 1.
Pisani, D. F. et al. "Differentiation of human adipose-derived stem cells into "brite" (brown-in-white) adipocytes" Frontiers in Endocrinology, Nov. 29, 2011, pp. 1-9, vol. 2, No. 87.
Unser, A. M et al. "Opportunities and Challenges in Three-dimensional Brown Adipogenesis of Stem Cells" *Biotechnology Advances,* Nov. 1, 2015, pp. 1-47, vol. 33, No. 6.
Written Opinion in International Application No. PCT/EP2016/066361, Sep. 22, 2016, pp. 1-7.

\* cited by examiner

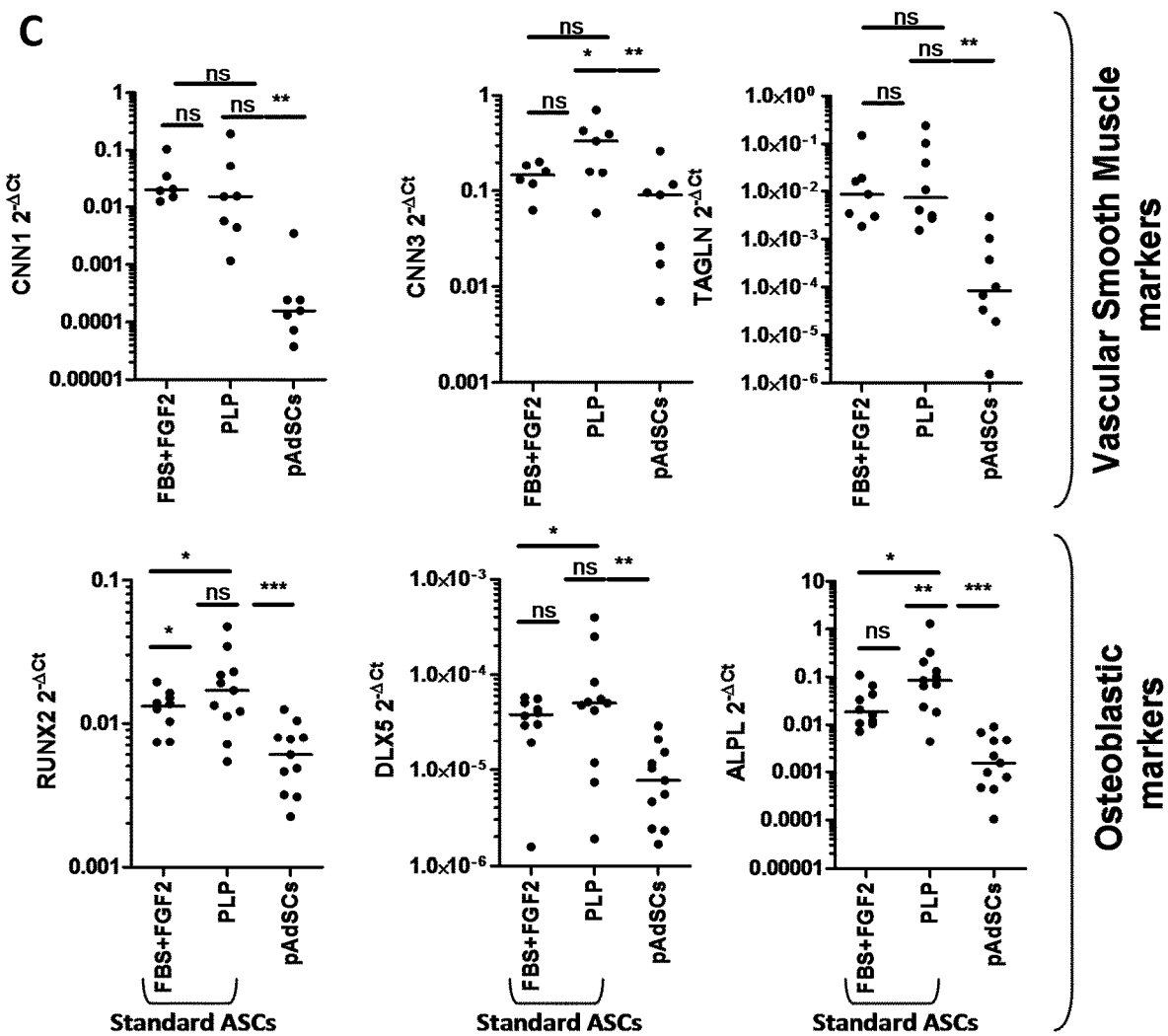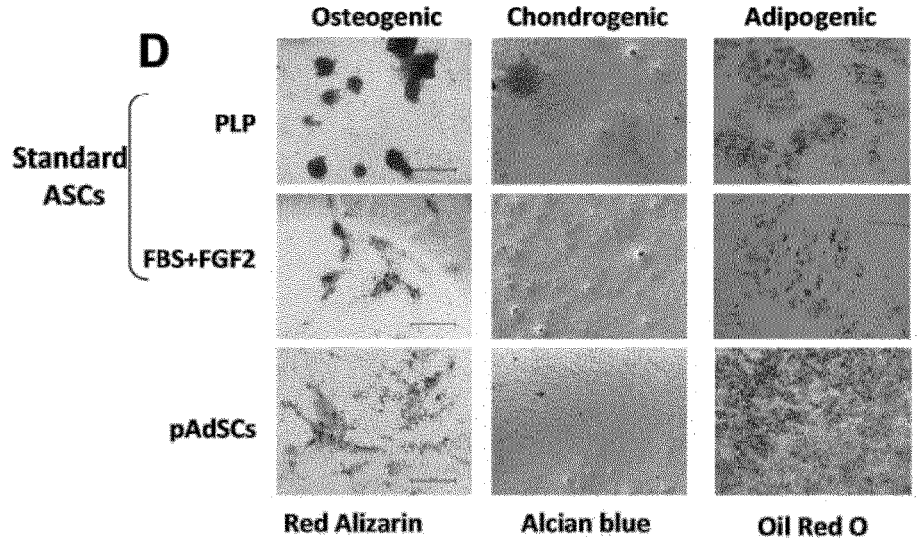
Figure 1 (following)

A

B

A

☐ Control
▨ BMP7
■ BMP4

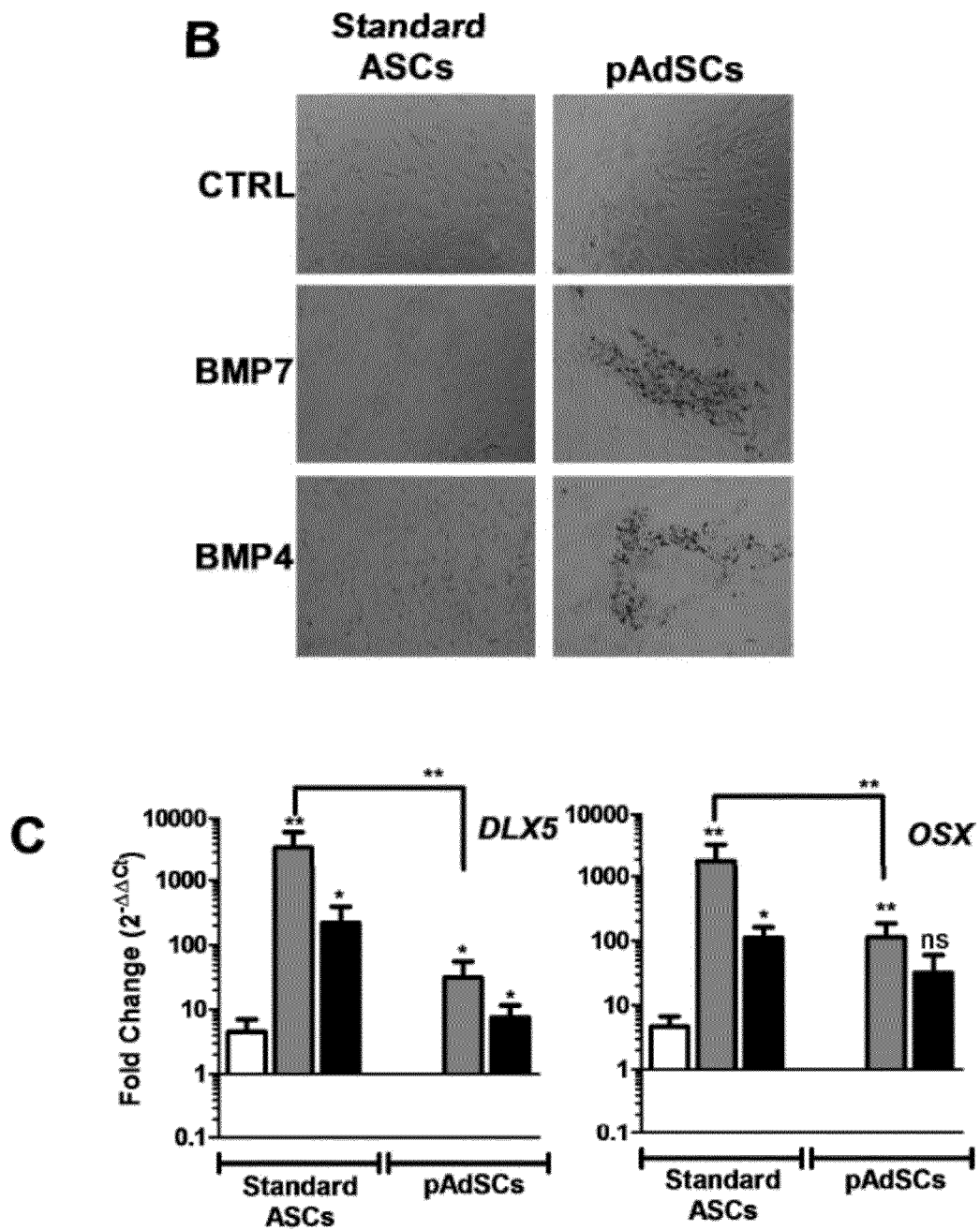
Figure 5 (following)

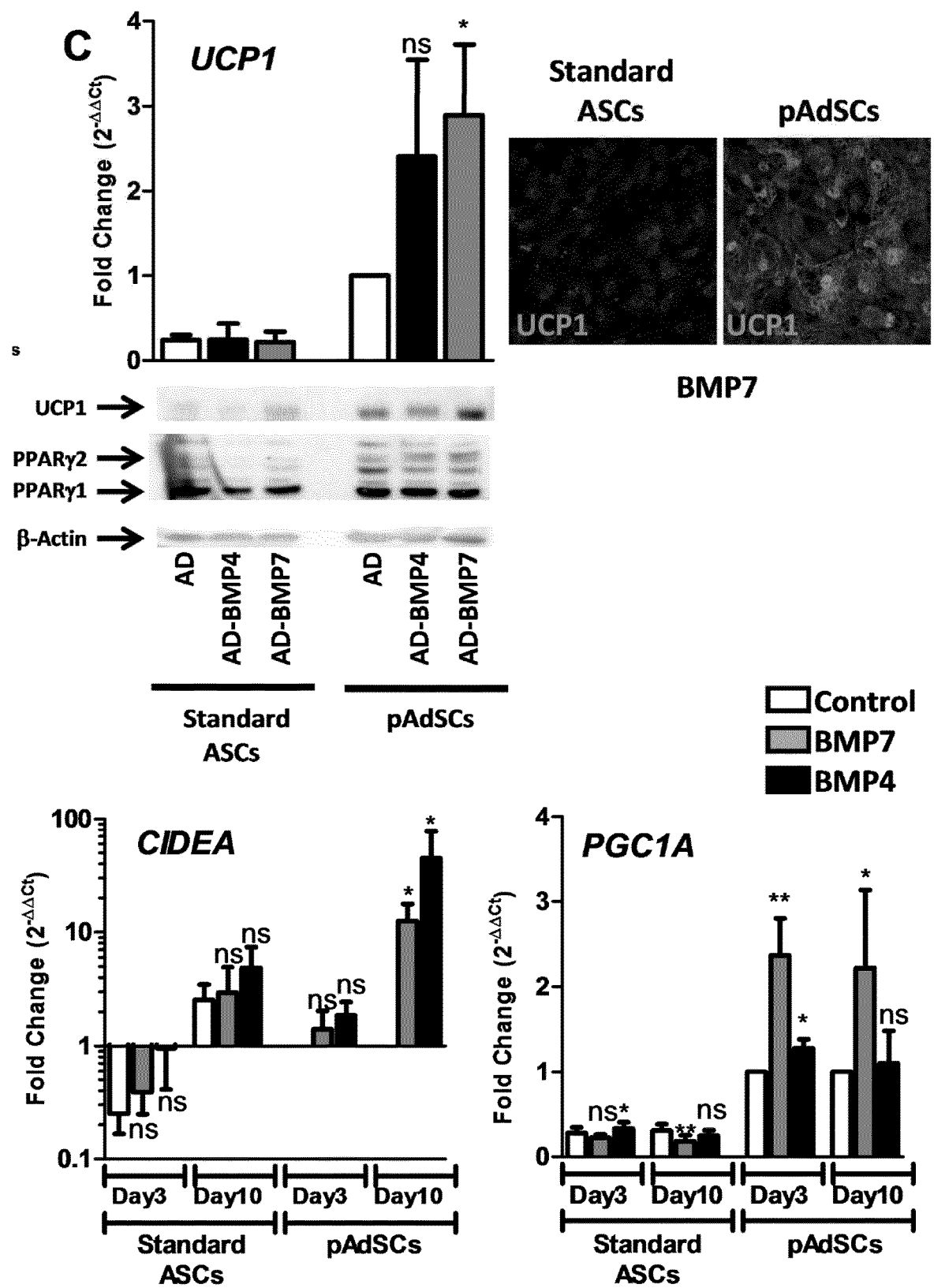
Figure 6 (Following)

B
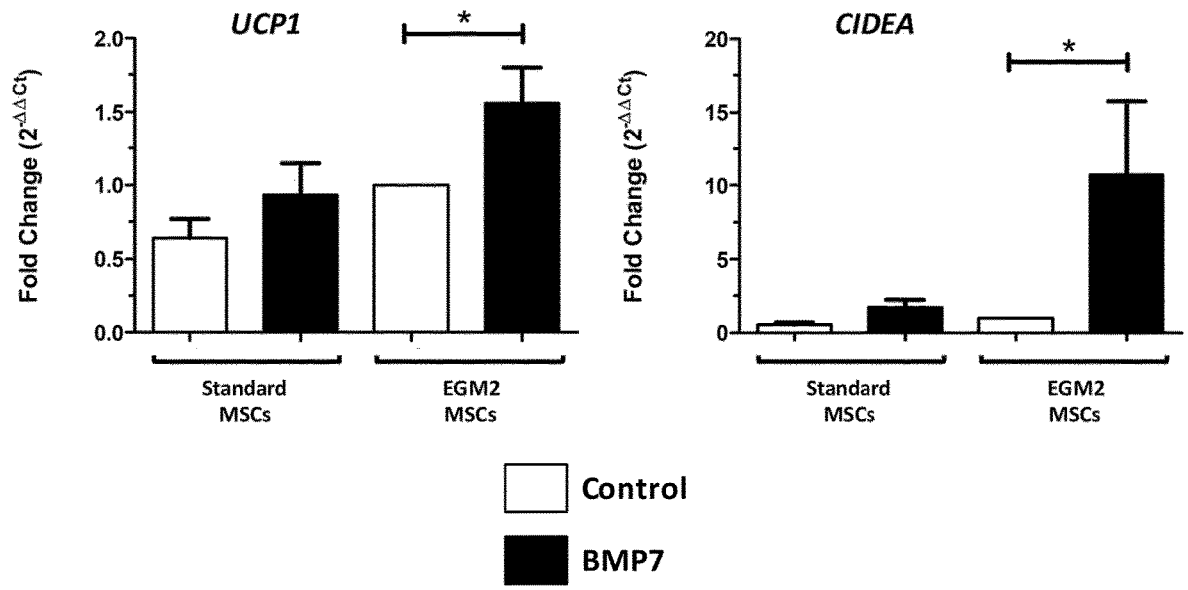
C
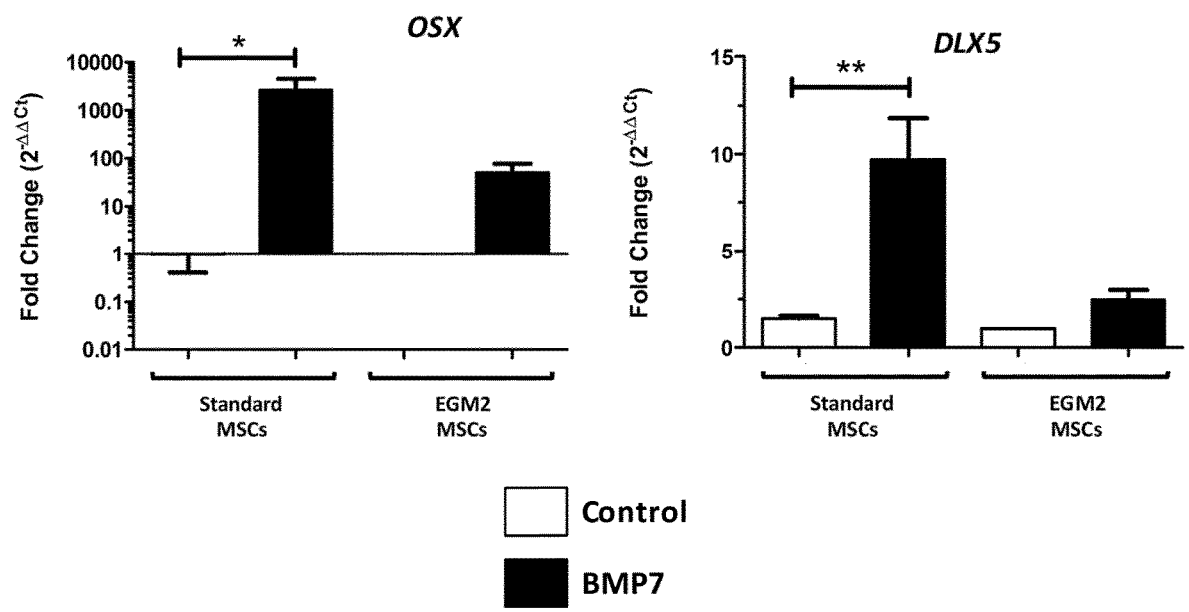
Figure 7 (Following)

METHOD FOR OBTAINING HUMAN BROWN/BEIGE ADIPOCYTES

CROSS-REFERENCE TO RELATED APPLICATION

This application is the U.S. national stage application of International Patent Application No. PCT/EP2016/066361, filed Jul. 8, 2016.

FIELD OF THE INVENTION

The present invention relates to the field of medicine, in particular to a method for obtaining brown/beige adipocytes from white adipose tissue or mesenchymal stem cells.

BACKGROUND OF THE INVENTION

Obesity, and metabolic disorders associated with obesity such as diabetes, cardiovascular diseases and hypertension, are a major global health concern. Over one billion adults are either overweight or obese and more than 150 million adults have diabetes, most of which is type 2 diabetes driven by obesity-associated insulin resistance (reviewed in Cypess A. M. and Kahn C. R., 2010, Curr. Opin. Endocrin. Diabetes & Obesity, 17, pp. 143-149). Twenty-five percent of children in the USA are also now overweight or obese leading to the appearance of type 2 diabetes in this previously unaffected population. These numbers are expected to increase worldwide by more than half again by the year 2025.

Obesity, which is generally associated with an abnormal accumulation of fat cells, develops when energy intake exceeds energy expenditure. Adipose tissues play an important role in obesity, insulin resistance and diabetes. Two main types of adipose tissues are present in mammals: white adipose tissue (WAT), which is the primary site of depot of triglycerides and release of fatty acids, and brown adipose tissue (BAT), which is specialized in thermogenic energy expenditure through the expression of uncoupling protein-1 (UCP-1).

White fat cells, also known as white adipose tissue (WAT) cells, are characterised by a thin ring of cytoplasm surrounding a lipid or fat droplet. WAT is found underneath the skin and provides heat insulation, cushioning against shock and jarring, and energy reserves. An average lean person has roughly 20 to 40 billion WAT cells. An obese person can have up to ten times more WAT than the average lean person.

Energy expenditure for thermogenesis in BAT serves either to maintain body temperature in the cold or to waste food energy. It has roles in thermal balance and energy balance, and when defective, is usually associated with obesity. Indeed, BAT is typically atrophied in obese animals. The importance of BAT in overall energy homeostasis is also underscored by the finding that ablation of BAT in mice results in severe obesity accompanied by insulin resistance, hyperglycemia, hyperlipidemia, and hypercholesterolemia (Lowell at al., 1993, Nature 366(6457):740-2; Hamann et al., 1995, Diabetes, 44(1 1): 1266-73; Hamann et al., 1996, Endocrinology 137(1):21-9).

BAT is abundant in rodents and human neonates but adult humans possess very little BAT and amounts decrease with aging. During the last few years, comparisons between WAT and BAT have led to the concept that white and brown adipocytes have distinct lineages (Timmons J A et al., 2007, Proc Natl Acad Sci U S A, 13;104(11):4401-6). The brown adipocytes originate from progenitor cells common to the myocyte lineage and characterized by the expression of MYF5 (Seale P et al., 2008, Nature, 21; 454(7207):961-7.). Recently, a third type of fully differentiated adipocyte has emerged: the brown in white adipocyte, which has been defined as brite (Petrovic Net al., 2010, J. Biol. Chem., 285(10): 7153-7164) or beige (Ishibashi J, Seale P, 2010, Science, 28; 328(5982):1113-4.). It shares a subset of features common to brown adipocytes such as the expression of uncoupling protein 1 (UCP1). Beige adipocytes appear in mice, in some "classical" WAT depots, under long-term PPARy agonist treatment (Petrovic N. et al., 2010) or beta-3 adrenergic receptor stimulation (Seale P et al., 2008). Such conditions have been associated with resistance to diet-induced obesity and metabolic alterations.

No data are yet available in humans concerning the presence and the role played by brite/beige adipocytes in the distinct WAT locations. Whether white and beige adipocytes share common progenitor cells (Lee Y H et al., 2012, Adipocyte, 1(4):230-236) and/or originate from the trans-differentiation of white adipocytes into brown-like adipocytes (Barbatelli G et al., 2010, 298(6):E1244-53) remains to be clearly established. Recently, it has been proposed that all adult human BAT are beige, rather than classical BAT (Wu et al., 2012, Cell, 150:1-11).

Because the amount of brown/beige cells in both rodents and humans is inversely correlated with obesity, it is strongly suggested that methods to increase brown/beige cell number in individuals might be a strategy to limit obesity and obesity-associated pathologies. Indeed, increasing the relative proportion of brown/beige adipocytes may increase whole body energy expenditure and therefore prevent the development of obesity.

Accordingly, a therapeutically proposal would be to introduce brown/beige adipocytes into adult humans to combat obesity. In that perspective, few reports have described methods for obtaining brown-like adipocytes. However, authors used specific stem cells notably those from pluripotent stem cells such as induced pluripotent stem cells (iPS cells) or those from cell lines (hMADs: human multipotent adipose-derived). iPS cells are generating after genetic modifications and are more related to embryonic development than brown/beige adipose tissue formation in adult. The genetic modifications necessitate huge safety due to tumorogenic properties of iPS cells. Concerning hMADs, they have been derived from very young donors (no hMAD was obtained from adult adipose tissue), and selected by bio-engineering procedures and are consequently not physiologically relevant for adult adipose tissue and the mechanisms regulating its biology. Thus, there is still a strong need to develop a reliable method to produce brown/beige adipocytes from human adult samples and/or primary cells.

SUMMARY OF THE INVENTION

The objective of the present invention is to propose a new method of producing adipogenic progenitors from human white adipose tissue or mesenchymal stem cells and further differentiating them into functional brown/beige adipocytes.

Accordingly, in a first aspect, the present invention concerns a method, preferably an in vitro method, of producing brown/beige adipocytes comprising contacting cells selected from white adipose tissue cells and mesenchymal stem cells, with a differentiation medium comprising, or consisting essentially of, serum, a glucocorticoid and a mix of growth factors comprising a growth factor of the VEGF family, a growth factor of the EGF family, an insulin-like growth factor and a growth factor of the FGF family, until obtaining adipogenic progenitor cells, contacting said adipogenic progenitor cells with an adipogenic agent until obtaining brown/beige adipocytes, and optionally recovering said brown/beige adipocytes.

Preferably, cells contacted with the differentiation medium are white adipose tissue cells, more preferably subcutaneous white adipose tissue cells.

The differentiation medium may comprise
from about 0.1 ng/mL to about 20 ng/mL of a growth factor of the EGF family,
from about 0.1 ng/mL to about 20 ng/mL a growth factor of the FGF family,
from about 5 ng/mL to about 40 ng/mL of an insulin-like growth factor, and/or
from about 0.05 ng/mL to about 10 ng/mL, preferably from 0.05 ng/mL to about 5 ng/mL, of a growth factor of the VEGF family.

In particular, the growth factor of the EGF family may be selected from the group consisting of epidermal growth factor (EGF), heparin-binding EGF-like growth factor (HB-EGF), transforming growth factor-α (TGF-α), amphiregulin (AREG), epiregulin (EREG), epigen (EPGN), betacellulin (BTC) and neuregulin-1, -2, -3 and -4 (NRG1, 2, 3 and 4), preferably is EGF, the growth factor of the FGF family may be FGF1 or FGF2, preferably FGF2, the insulin-like growth factor may be selected from the group consisting of IGF-1, IGF-2, IGFL1, IGFL2, IGFL3 and IGFL4 and synthetic analogs thereof such as mecasermin or long(R3)-IGF-1, preferably is IGF-1 or an analog thereof, and/or the growth factor of the VEGF family may be selected from the group consisting of VEGF-A, preferably VEGF-A splice form $VEGF_{121}$, $VEGF_{145}$ or $VEGF_{165}$, VEGF-B, VEGF-C, VEGF-D and PGF, more preferably is VEGF, in particular VEGF-A. Preferably, the mix of growth factors comprises, or consists of, (i) VEGF-A, preferably $VEGF_{165}$, (ii) EGF, (iii) IGF-1 or an analog thereof, preferably long(R3)-IGF-1, and (iv) FGF2. Preferably, the differentiation medium comprises from about 0.5% to about 10% serum, and/or from about 0.05 μg/mL to about 5 μg/mL of a glucocorticoid.

Preferably, the glucocorticoid is selected from the group consisting of hydrocortisone, dexamethasone, betamethasone and cortivazol, more preferably is hydrocortisone.

Preferably, the serum is fetal bovine serum.

Preferably, the serum is fetal bovine serum and the glucocorticoid is hydrocortisone.

The differentiation medium may further comprise a free-radical scavenger or anti-oxidant, preferably ascorbic acid.

The adipogenic agent may be selected from the group consisting of insulin or analogs thereof, non-selective phosphodiesterase (PDE) inhibitors, beta-adrenergic agonists, thiazolidinediones, glucocorticoids, Bone Morphogenetic Proteins (BMPs), derivatives and mixtures thereof.

Preferably, the adipogenic agent is a mix comprising one or several adipogenic agents selected from the group consisting of insulin, dexamethasone, indomethacin, IBMX, rosiglitazone, BMP4 and BMP7. More preferably, the adipogenic agent comprises a Bone Morphogenetic Protein, preferably selected from BMP4 and BMP7, more preferably BMP7, and optionally insulin. Even more preferably, the adipogenic agent is a Bone Morphogenetic Protein, preferably selected from BMP4 and BMP7, more preferably is BMP7.

In some embodiments, white adipose tissue cells or mesenchymal stem cells may be contacted with the differentiation medium in a culture system enabling 3D spheroid formation, thereby producing spheroids of adipogenic progenitor cells. Preferably, spheroids of adipogenic progenitor cells may be transferred into a 3D culture matrix mimicking the extracellular matrix and allowing three-dimensional growth, before to be contacted with the adipogenic mix. In particular, the 3D culture matrix may be microbeads/droplets of 3D culture hydrogel, preferably microbeads/droplets of matrigel. Brown/beige adipocytes obtained by the method of the invention may be recovered from said 3D culture matrix, i.e. the 3D culture matrix is removed, or may be still embedded in the 3D culture matrix.

In another aspect, the present invention relates to a population of brown/beige adipocytes obtained by the method according to the invention. Preferably, in said population, brown/beige adipocytes are in the form of organoids and/or comprise unilocular adipocytes. Brown/beige adipocytes may also be comprised/embedded in a 3D culture matrix.

In a further aspect, the present invention relates to a pharmaceutical composition comprising a population of brown/beige adipocytes according to the invention and a pharmaceutically acceptable carrier, for use in a cell-based therapy.

Preferably, the pharmaceutical composition is for use in the treatment of obesity and/or obesity-associated diseases, preferably selected from the group consisting of type 2 diabetes, impaired glucose tolerance, insulin resistance, dyslipidemia, hypertension and cardiovascular diseases.

In another aspect, the present invention also relates to an in vitro method of screening compounds stimulating the shifting of white adipocytes to brown/beige adipocytes, comprising
contacting cells selected from white adipose tissue cells and mesenchymal stem cells, with a differentiation medium comprising, or consisting essentially of, serum, a glucocorticoid, a free-radical scavenger or anti-oxidant, and a mix of growth factors comprising a growth factor of the VEGF family, a growth factor of the EGF family, an insulin-like growth factor and a growth factor of the FGF family, until obtaining adipogenic progenitor cells,
contacting said adipogenic progenitor cells with a candidate compound, and
assessing the obtaining of brown/beige adipocytes,
wherein the candidate compound stimulates the shifting of white adipocytes to brown/beige adipocytes if brown/beige adipocytes are obtained.

The present invention further relates to an in vitro method of identifying compounds capable of increasing the thermogenic program of brown/beige adipocytes, comprising
contacting cells selected from white adipose tissue cells and mesenchymal stem cells, with a differentiation medium comprising, or consisting essentially of, serum, a glucocorticoid and a mix of growth factors comprising a growth factor of the VEGF family, a growth factor of the EGF family, an insulin-like growth factor and a growth factor of the FGF family, until obtaining adipogenic progenitor cells,
contacting said adipogenic progenitor cells with an adipogenic agent until obtaining brown/beige adipocytes, and optionally recovering said brown/beige adipocytes,
contacting said brown/beige adipocytes with a candidate compound, and
monitoring the effect of said candidate compound on the activity of brown/beige adipocytes.

The present invention further relates to a kit for the production of brown/beige adipocytes comprising (i) a differentiation medium comprising, or consisting essentially of, serum, a glucocorticoid and a mix of growth factors comprising a growth factor of the VEGF family, a growth factor of the EGF family, an insulin-like growth factor and a growth factor of the FGF family, (ii) one or more adipogenic agents. Preferably, the kit further comprises a 3D culture system, preferably comprising one or several ultra-low attachment plates and a 3D culture matrix. The present invention also relates to the use of a kit of the invention to produce brown/beige adipocytes according to the method of the invention.

DETAILED DESCRIPTION OF THE INVENTION

Figure 1:
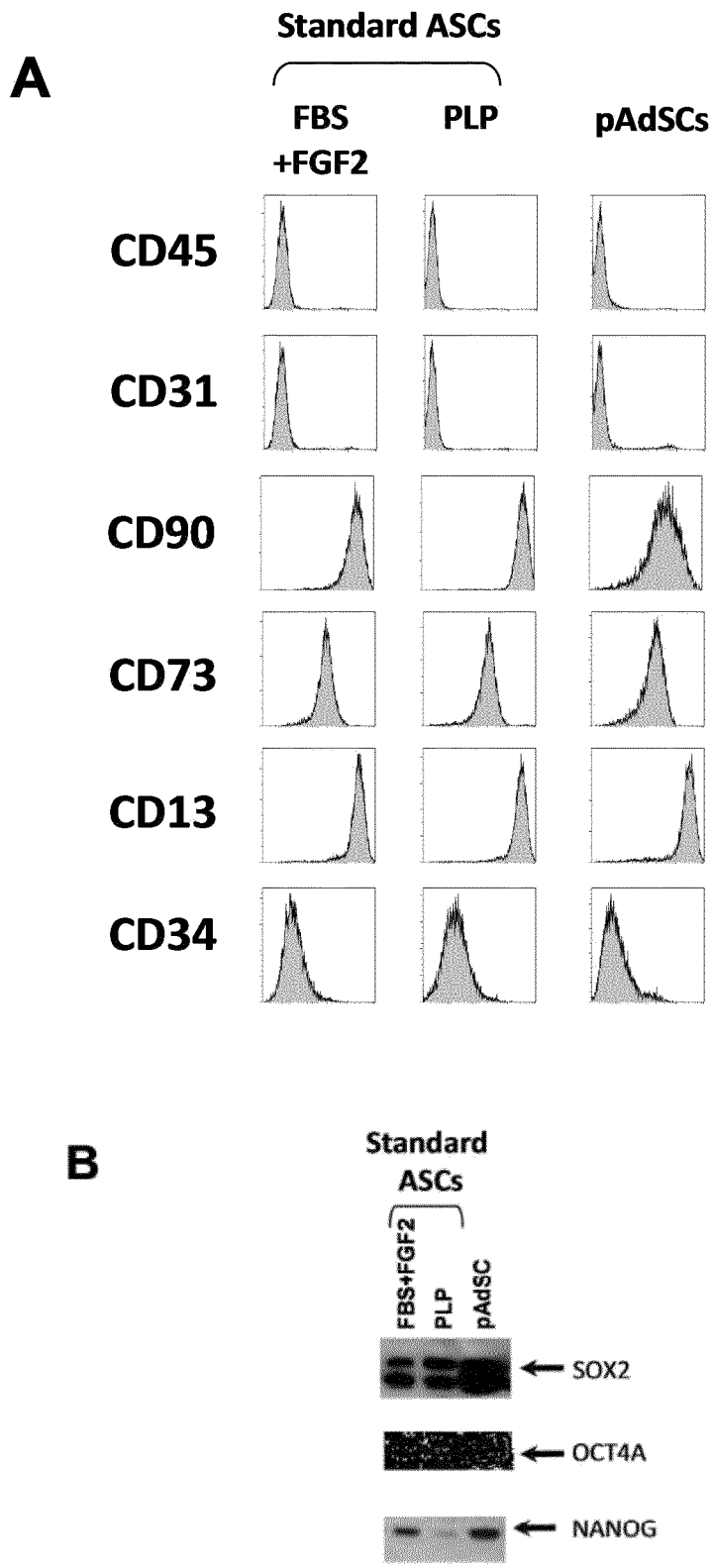
FIG. 1: Perivascular adipose tissue-derived stem/progenitor cells (pAdSCs) are immature and adipogenic. Cells from white adipose tissue were cultured in different media: standard media (FBS+FGF2 or platelet lysate-enriched plasma, PLP) or ECGM2 medium (expansion of pAdSCs). After expansion, cells from these culture conditions were subjected to phenotypic analysis by using flow cytometer (A): Endothelial (CD31) and hematopoietic (CD45) markers were not found whereas ASCs markers (CD90, CD73, CD13 and CD34) were detected. (B): stemness markers were all found in pAdSCs and at a lesser extent in standard ASCs. (C): before differentiation, QRT-PCR data showed that standard ASCs expressed osteoblastic and vascular smooth muscle lineage markers whereas those markers were significantly down regulated in pAdSCs. (D): whatever the condition (standard media or ECGM2), cells were able to generate osteoblasts (red alizarin), chondroblasts (Alcian blue) and adipocytes (Oil red O) after induction of differentiation, but pAdSCs were more prone to differentiate into adipocytes.

The inventors have developed a new method, simple and fast, for producing brown/beige adipocytes from human adult white adipose tissue (WAT). They surprisingly found that culturing WAT in a culture medium optimized for the cultivation of endothelial cells from large blood vessels, such as ECGM2 medium, results in a population of stem/progenitor cells exhibiting properties that are distinct from progenitor cell populations usually isolated from WAT. Indeed, this adipogenic progenitor population, also named herein pAdSCs, has a lower expression of osteoblastic, chondroblastic, and smooth muscle cell lineage markers and can differentiate very efficiently into functional brown/beige adipocytes upon physiological differentiation factors such as BMP4 and BMP7. In addition, their overall transcriptome data are quite different to those from cells deriving from standard conditions. Similar results were obtained from mesenchymal stem cells from bone marrow.

Accordingly, in a first aspect, the invention relates to a method of producing brown/beige adipocytes comprising contacting cells selected from white adipose tissue cells and mesenchymal stem cells, with a differentiation medium comprising, or consisting essentially of, serum, a glucocorticoid and a mix of growth factors comprising a growth factor of the VEGF family, a growth factor of the EGF family, an insulin-like growth factor and a growth factor of the FGF family, until obtaining adipogenic progenitor cells.

Preferably, the method further comprises contacting said adipogenic progenitor cells with an adipogenic agent, preferably a physiological adipogenic agent, until obtaining brown/beige adipocytes.

Optionally, the method further comprises recovering said brown/beige adipocytes.

The methods of the invention, as disclosed below, may be in vivo, ex vivo or in vitro methods, preferably in vitro methods.

As used herein, the term "brown/beige adipocytes" refers to cells which have the characteristics of brown or beige fat, preferably human brown or beige fat. In particular, this term refers to adipocytes that express the "thermogenin" protein or "uncoupled protein-1" (UCP1, Gene ID: 7350), i.e. an uncoupling protein found in the mitochondria of brown adipocytes that generate heat by non-shivering thermogenesis, PPARγ2 (Peroxisome Proliferator-Activated Receptor gamma 2, Gene ID: 5468), CIDEA (Cell death-inducing DFFA-like effector A, Gene ID: 1149), LPL (Lipoprotein Lipase, Gene ID: 4023), ADIPOQ (Adiponectin C1Q and collagen domain containing, Gene ID: 9370), PGC1α (or PPARGC1A, Peroxisome Proliferator-Activated Receptor Gamma Coactivator 1 alpha, Gene ID : 10891), CEBPA (CCAAT/enhancer binding protein (C/EBP), alpha; Gene ID: 1050) and AP2 (or FABP4, Fatty acid binding protein 4; Gene ID: 2167).

Cells contacted with the differentiation medium are selected from white adipose tissue cells and mesenchymal stem cells. Cells are preferably mammal cells, and more preferably human cells. In preferred embodiment, cells are obtained from human of any age, preferably from an adult human.

In an embodiment, cells contacted with the differentiation medium are white adipose tissue cells. As used herein, the term "white adipose tissue cells" refers to cells present in white fat, preferably in human white fat, more preferably in adult human white fat. Two kinds of adipose tissue are found in mammals: white adipose tissue (WAT) and brown adipose tissue (BAT). WAT adipocytes contain few mitochondria and a single large fat droplet, which forces the nucleus to be squeezed into a thin rim at the periphery. They further secrete several hormones, including leptin and adiponectin. WAT adipocytes typically express RETN (Resistin, Gene ID: 56729). In mammals, WAT cells are located essentially beneath the skin (subcutaneous WAT), around internal organs (visceral WAT), in bone marrow (yellow bone marrow WAT) and in breast tissues. Preferably, WAT cells used in the present invention are subcutaneous WAT cells, more preferably human subcutaneous WAT cells, and even more preferably adult human subcutaneous WAT cells. Preferably, subcutaneous WAT cells used in the present invention comprise, or consist of, the stromal vascular fraction (SVF) of subcutaneous adipose tissue.

In another embodiment, cells contacted with the differentiation medium are mesenchymal stem cells (MSC) from bone marrow. As used herein, the term "mesenchymal stem cells" or "MSC" refers to multipotent stromal cells that can differentiate into a variety of cell types, including osteoblasts, chondrocytes, myocytes and adipocytes. MSC used in the present invention are preferably human MSC, and in particular human adult mesenchymal stem cells. MSC may be obtained from a subject by any method known by the skilled person, in particular from bone marrow using a colony-forming unit-fibroblasts (CFU-F) approach, where raw unpurified bone marrow or ficoll-purified bone marrow mononuclear cell are plated directly into cell culture plates or flasks, and MSC are selected by adhesion to tissue culture plastic contrary to red blood cells or haematopoietic progenitors. MSC typically express CD44, CD29, CD73, CD105 and SSEA4.

WAT cells or MSC may be primary or secondary cells. The term "primary cell" includes cells present in a suspension of cells isolated from a mammalian tissue source (prior to their being plated, i.e., attached to a tissue culture substrate such as a dish or flask), cells present in an explant derived from tissue, both of the previous types of cells plated for the first time, and cell suspensions derived from these plated cells. The term "secondary cell" refers to cells at all subsequent steps in culturing, in particular cells that have been passaged one or more times. Preferably, cells used in the method of the present invention are primary cells.

The method of the invention may further comprise providing WAT cells or mesenchymal cells, in particular from a mammal, preferably from a human.

WAT cells may be obtained from a subject by any method known by the skilled person, in particular by liposuction or by lipodectomia. Cells were detached enzymatically.

MSC may be obtained from a subject by any method known by the skilled person, e.g. from bone marrow by using aspiration or from femoral head mechanical extraction.

The method of the invention comprises contacting WAT cells or MSC with a differentiation medium comprising, or consisting essentially of, serum, a glucocorticoid and a mix of growth factors comprising a growth factor of the VEGF family, a growth factor of the EGF family, an insulin-like growth factor and a growth factor of the FGF family, until obtaining adipogenic progenitor cells.

As used herein, the term "consisting essentially of means that the differentiation medium does not comprise any other active substance that has an effect on the differentiation of cells but may comprise further compounds allowing maintenance or growth of cells such as nutrients, buffers, organic salts, antibiotics, etc.

The serum contained in the differentiation medium is preferably from animal origin, more preferably is fetal bovine serum or a synthetic alternative. The medium may comprise from about 0.5% to about 10% serum, preferably from about 1% to about 5% serum, more preferably about 2% serum.

As used in this specification, the term "about" refers to a range of values±10% of the specified value. Preferably, the term "about" refers to a range of values±5% of the specified value.

The differentiation medium comprises at least one glucocorticoid, i.e. a steroid hormone that bind to the glucocorticoid receptor. Examples of glucocorticoids include, but are not limited to, dexamethasone, betamethasone, cortivazol and hydrocortisone. Preferably, the glucocorticoid is hydrocortisone. The medium may comprise from about 0.05 μg/mL to about 5 μg/mL of glucocorticoid, preferably about 0.1 μg/mL to about 2 μg/mL of a glucocorticoid, more preferably about 0.2 μg/mL of a glucocorticoid.

Preferably, the differentiation medium comprises fetal bovine serum and hydrocortisone.

The differentiation medium comprises a mix of growth factors comprising at least one growth factor of the VEGF family, at least one growth factor of the EGF family, at least one insulin-like growth factor and at least one growth factor of the FGF family. Preferably, the mix consists of a growth factor of the VEGF family, a growth factor of the EGF family, an insulin-like growth factor and a growth factor of the FGF family.

As used herein, the term "growth factor of the VEGF family" refers to growth factors belonging to the family of the Vascular Endothelial Growth Factor such as VEGF-A, VEGF-B, VEGF-C, VEGF-D and PGF (Placenta Growth Factor). Preferably, this term refers to VEGF-A. Human VEGF-A gene encodes five isoforms of 121, 145, 165, 189 and 209 amino-acids (Neufeld et al., 1999, The FASEB Journal, vol. 13, no. 1, 9-22). Preferably, the mix comprises a secreted VEGF-A splice form, i.e. $VEGF_{121}$, $VEGF_{145}$ or $VEGF_{165}$. More preferably, the growth factor of the VEGF family is able to selectively bind to the VEGF-R1, R2, R3 and neuropilin-1 and neuropilin-2 co-receptors. Even more preferably, the growth factor of the VEGF family is $VEGF_{165}$. The differentiation medium may comprise from about 0.05 ng/mL to about 10 ng/mL of a growth factor of the VEGF family, preferably about 0.1 ng/mL to about 5 ng/mL, more preferably about 0.5 ng/mL.

As used herein, the term "growth factor of the EGF family" refers to growth factors belonging to the family of the Epidermal Growth Factor such as epidermal growth factor (EGF), heparin-binding EGF-like growth factor (HB-EGF), transforming growth factor-α (TGF-α), amphiregulin (AREG), epiregulin (EREG), epigen (EPGN), betacellulin (BTC), neuregulin-1, -2, -3 and -4 (NRG1, 2, 3 and 4). Preferably, the growth factor of the EGF family is EGF. The differentiation medium may comprise from about 0.1 ng/mL to about 20 ng/mL of a growth factor of the EGF family, preferably about 1 ng/mL to about 10 ng/mL, more preferably about 5 ng/mL.

As used herein, the term "insulin-like growth factor" refers to hormones similar in molecular structure to insulin. In particular, the insulin-like growth factor may be selected from the group consisting of insulin-like growth factor 1 (IGF-1 or somatomedin C), insulin-like growth factor 2 (IGF-2), IGFL1, IGFL2, IGFL3 and IGFL4 and synthetic analogs thereof. Preferably, the insulin-like growth factor is IGF-1 or a synthetic analog thereof such as mecasermin or long(R3)-IGF-1 (Hill et al. Domest Anim Endocrinol. 1999 May;16(4):219-29). The differentiation medium may comprise from about 5 ng/mL to about 40 ng/mL of an insulin-like growth factor, preferably about 10 ng/mL to about 30 ng/mL, more preferably about 20 ng/mL.

As used herein, the term "growth factor of the FGF family" refers to growth factors belonging to the family of Fibroblast Growth Factors. Preferably, the growth factor of the FGF family is FGF1 (acidic fibroblast growth factor) or FGF2 (basic fibroblast growth factor, bFGF or FGF-(3). More preferably, the growth factor of the FGF family is FGF2. The differentiation medium may comprise from about 0.1 ng/mL to about 20 ng/mL of a growth factor of the FGF family, preferably about 1 ng/mL to about 15 ng/mL, more preferably about 10 ng/mL.

In a particular embodiment, the mix of growth factors comprises, or consists of, (i) VEGF-A, preferably $VEGF_{165}$, (ii) EGF, (iii) IGF-1 or an analog thereof, preferably long (R3)-IGF-1, and (iv) FGF2.

In a particular embodiment, the differentiation medium comprises, or consists essentially of,
 from about 0.5% to about 10% serum, preferably about 1% to about 5% serum, more preferably about 2% serum;
 from about 0.05 μg/mL to about 5 μg/mL of glucocorticoid, preferably about 0.1 μg/mL to about 2 μg/mL of a glucocorticoid, more preferably about 0.2 μg/mL of a glucocorticoid;
 from about 0.1 ng/mL to about 20 ng/mL of a growth factor of the EGF family, preferably about 1 ng/mL to about 10 ng/mL, more preferably about 5 ng/mL;
 from about 0.1 ng/mL to about 20 ng/mL of a growth factor of the FGF family, preferably about 1 ng/mL to about 15 ng/mL, more preferably about 10 ng/mL;
 from about 5 ng/mL to about 40 ng/mL of an insulin-like growth factor, preferably about 10 ng/mL to about 30 ng/mL, more preferably about 20 ng/mL; and/or
 from about 0.05 ng/mL to about 10 ng/mL of a growth factor of the VEGF family, preferably about 0.1 ng/mL to about 5 ng/mL, more preferably about 0.5 ng/mL.

Preferably, the serum is fetal bovine serum, the glucocorticoïd is hydrocortisone and the mix of growth factor comprises, or consists of, VEGF-A, preferably $VEGF_{165}$, (ii) EGF, (iii) IGF-1 or an analog thereof, preferably long(R3)-IGF-1, and (iv) FGF2. More preferably, the serum is fetal bovine serum, the glucocorticoïd is hydrocortisone and the mix of growth factor consists of $VEGF_{165}$, EGF, long(R3)-IGF-1, and FGF2.

Optionally, the differentiation medium may further comprise at least one free-radical scavenger and/or anti-oxidant, i.e. a compound that scavenges reactive oxygen species before they can damage cells and that maintains proteins in their reduced state. Examples of free-radical scavenger or anti-oxidant include, but are not limited to, vitamin C (ascorbic acid), vitamin A and vitamin E and their derivatives, glutathione, N-acetylcysteine, catalases, superoxide dismutases and peroxidases. Preferably, the scavenger or anti-oxidant is ascorbic acid. The differentiation medium may comprise from about 0.2 μg/mL to about 10 μg/mL of radical scavenger or anti-oxidant, preferably from about 0.5 μg/mL to about 5 μg/mL, more preferably about 1 μg /mL.

In a preferred embodiment, the differentiation medium is the medium ECGM2 (PromoCell, Heidelberg, Germany).

Cells are contacted with the differentiation medium until obtaining adipogenic progenitor cells.

Adipogenic progenitor cells obtained according to the method of the invention strongly express the stemness factors NANOG (Nanog homeobox, Gene ID: 79923), OCT4 (Octamer-binding transcription factor 4, Gene ID: 5460) and SOX2 (SRY (sex determining region Y)-box 2, Gene ID: 6657) and weakly express osteoblastic (such as RUNX2, DLX5 and ALPL), chondroblastic and smooth muscle cell (such as ACTA2, CNNI, CNN3 and TAGLN) lineage markers, in particular in comparison with standard adipose derived stromal cells (ASCs) obtained by culturing WAT cells in standard conditions, e.g. in a culture medium comprising fetal bovine serum and FGF2 or comprising plasma-derived platelet lysate (PLP). As shown in the experimental section, the inventors demonstrated that adipogenic progenitor cells obtained by contacting WAT cells or MSC with the differentiation medium defined above, are more prone to form adipocytes whereas ASCs are more potent to give rise to osteoblasts and chondroblasts. Preferably, as shown in FIG. 1, adipogenic progenitor cells express CD90, CD73, CD13 and CD34 and do not express CD31 and CD45.

In a particular embodiment, WAT cells or MSC are contacted with the differentiation medium for at least 3 days, preferably for 7 to 21 days, more preferably for 3 to 14 days.

Cells may be contacted with the differentiation medium in any suitable cell culture system well-known and easily chosen by the skilled person, in particular any system adapted to the culture of adherent cells such as culture dishes or flasks or any system enabling 3D spheroid formation such as ultra-low attachment plates or agarose-coated well plates.

As demonstrated in the experimental section, the inventors showed that 3D spheroid cultures provide better results than 2D monolayer cultures. Thus, in a preferred embodiment, cells are contacted with the differentiation medium in a 3D spheroid culture system. Culture systems enabling 3D spheroid formation are well-known by the skilled person. Preferably, this system is a culture in ultra-low attachment plates. As used herein, the term "spheroid" refers to an aggregate, cluster or assembly of cells cultured to allow three-dimensional growth in contrast to the two-dimensional growth of cells in either a monolayer or cell suspension (cultured under conditions wherein the potential for cells to aggregate is limited).

The medium may be changed regularly, preferably daily, and cells may be passaged to prevent confluency. These procedures are well known from the man skilled in the art.

Adipogenic progenitor cells are then contacted with an adipogenic mix comprising one or several adipogenic agents to obtain brown/beige adipocytes.

As used herein, the term "adipogenic agent" or "browning agent" refers to an agent that is capable of inducing the differentiation of adipogenic progenitor cells into brown/beige adipocytes. Typically, an agent is deemed to induce brown/beige adipogenesis if it leads to an increase in the expression of the gene encoding UCP1. Adipogenic agents have been already described in the art. Examples of adipogenic agents include, but are not limited to, insulin and analogs thereof such as IGF-1, non-selective phosphodiesterase (PDE) inhibitors, beta-adrenergic agonists, thiazolidinediones, glucocorticoids, bone morphogenetic proteins (BMPs), derivatives or mixture thereof.

Non-selective PDE inhibitors are drugs that block two or more of the five subtypes of the enzyme phosphodiesterase (PDE). Examples of non-selective PDE inhibitors include, but are not limited to, indomethacin, 3-isobutyl-1-methyl-xanthine (IBMX), paraxanthine, pentoxifylline, theobromine, theophylline, methylated xanthines, caffeine and aminophylline. Preferably, the non-selective PDE inhibitor is indomethacin and/or IBMX, more preferably is indomethacine.

Beta-adrenergic agonists are compounds that activate adrenaline (also known as epinephrine) beta receptors. Example of beta-adrenergic agonists include, but are not limited to, adrenalin, noradrenaline, salbutamol, procaterol, dobutamine, terbutaline and isoproterenol.

Thiazolidinediones are PPARγ receptor agonists. Examples of thiazolidinediones include, but are not limited to, rosiglitazone, pioglitazone and troglitazone. Preferably, the thiazolidinedione is rosiglitazone.

Glucocorticoids are agents that bind to the glucocorticoid receptor. Examples of glucocorticoids include, but are not limited to, dexamethasone, betamethasone, cortivazol and hydrocortisone. Preferably, the glucocorticoid is dexamethasone.

Bone Morphogenetic Proteins (BMPs) are members of the transforming growth factor superfamily that are involved in multiple key steps of embryonic development as well as throughout life (Kishigami and Mishina, 2005, Cytokine Growth Factor. Rev. 16:265-278). Example of BMPs include, but are not limited to, BMP1, BMP2, BMP3, BMP4, BMP5, BMP6, BMP7, BMP8 and BMP9. Preferably, the BMP is BMP4 and/or BMP7. More preferably, the BMP7.

In an embodiment, the adipogenic mix comprises one or several adipogenic agents selected from the group consisting of insulin, dexamethasone, indomethacin, IBMX, rosiglitazone, BMP4 and BMP7.

In a particular embodiment, adipogenic progenitor cells are contacted with an adipogenic mix comprising a non-selective PDE inhibitor, a thiazolidinedione, insulin or an analog thereof, and a glucocorticoid. Preferably, the adipogenic mix comprises indomethacin, rosiglitazone, insulin and dexamethasone.

In this embodiment, the adipogenic mix may comprise
from 0.05 to about 1 mM of a non-selective PDE inhibitor, preferably indomethacin;
from 0.1 to about 10 µM of a thiazolidinedione, preferably rosiglitazone;
from 0.1 to about 10 µg/mL of insulin or an analog thereof, preferably insulin; and
from 0.1 to about 10 µM of glucocorticoid, preferably dexamethasone.

In another particular embodiment, adipogenic progenitor cells are contacted with one or several BMPs, preferably BMP4 and/or BMP7, more preferably BMP7. In particular, the adipogenic mix may comprise, or consist essentially of, one or several BMPs, preferably BMP4 and/or BMP7, more preferably BMP7. As used herein, the term "consist essentially of" means that the adipogenic mix does not comprise any other active substance that has an effect on the differentiation of adipogenic progenitor cells into brown/beige adipocytes.

In another particular embodiment, adipogenic progenitor cells are contacted with one or several BMPs, preferably BMP4 and/or BMP7, more preferably BMP7, and insulin. In particular, the adipogenic mix may comprise, or consist essentially of, one or several BMPs, preferably BMP4 and/or BMP7, more preferably BMP7, and insulin.

In this embodiment, the adipogenic mix may comprise from 1 to about 500 ng/mL of BMPs, in particular from 1 to about 500 ng/mL of BMP4 and/or from 1 to about 500 ng/mL of BMP7.

Optionally, the adipogenic mix may further comprise an adenylate cyclase activator, i.e. a molecule inducing an increase of cAMP intracellular levels. Examples of adenylate cyclase activators include, but are not limited to, forskolin, glucagon, prostaglandins D2, E1 and I2, carba-cyclin, dopamin, endothelin 1, L-epinephrin and parathyroid hormone. Preferably, the adenylate cyclase activator is forskolin. The adenylate cyclase activator may be added to the adipogenic mix from the beginning or after several days.

Adipogenic progenitor cells may be contacted with the adipogenic mix through the replacement of the culture medium with a fresh culture medium containing the adipogenic agents at the desired concentration. Alternatively, adipogenic agents are added to the culture medium serially (i.e. BMPs then adipogenic mix) or only BMPs.

Adipogenic progenitor cells may be contacted with the adipogenic mix in a 2D culture system or in a 3D culture system. In a preferred embodiment, differentiation of cells into adipogenic progenitor cells and contact of adipogenic progenitor cells with the adipogenic mix are performed in a 3D system. Preferably, before to be contacted with the adipogenic mix, spheroids of adipogenic progenitor cells are transferred into a 3D culture matrix mimicking the extracellular matrix and allowing three-dimensional growth. Such matrices are well known by the skilled person and include, but are not limited to, matrigel®, collagen, fibronectin, laminin, gelatin, alginate, alginate/matrigel®, methylcellulosis, collagen/matrigel® and hyaluronic acid hydrogels, as well as numerous commercially available systems. Preferably, spheroids of adipogenic progenitor cells are transferred into microbeads/droplets of 3D culture hydrogel, more preferably into microbeads/droplets of Matrigel®. As demonstrated in the experimental section, the use of a 3D culture system during the differentiation of adipogenic progenitor cells into brown/beige adipocytes, promotes the appearance of unilocular adipocytes and leads to the formation of organoids wherein endothelial cells are able to self-organize in networks with a tubular morphology. Preferably, this 3D system is maintained until obtaining brown/beige adipocytes. Optionally, brown/beige adipocytes may be recovered from the 3D culture matrix or may be used embedded in such matrix. In an embodiment, brown/beige adipocytes may be recovered from the 3D culture matrix by removing said matrix and recovering cells or organoids. 3D culture matrices may be eliminated by any method known by the skilled person. In another embodiment, brown/beige adipocytes are recovered still embedded in the matrix.

Adipogenic progenitor cells are contacted with adipogenic agents for at least 3 days, preferably from 3 to 21 days, more preferably for 3 to 7 days. The skilled person can easily determine the duration of this step by assessing the expression of markers specific of brown/beige adipocytes, i.e. UCP1, PPARγ2, CIDEA, LPL, ADIPOQ, PGC1α, CEBPA and AP2. The medium may be changed regularly, preferably daily, and cells may be passaged to prevent confluency. These procedures are well known from the man skilled in the art.

Optionally, the method may further comprise a step of multiplication of adipogenic progenitor cells before differentiation into brown/beige adipocytes and/or a step of multiplication of brown/beige adipocytes produced by the method. Adipogenic progenitor cells and/or brown/beige adipocytes may thus be allowed to undergo several rounds of doubling, in particular to provide a sufficient number to be administered to a subject in need thereof or to establish a stable cell line.

Optionally, the method of the invention may also comprise testing the characteristics and functionality of obtained brown/beige adipocytes. The characteristics may be assessed by determining the expression of specific brown/beige adipocyte markers such as UCP1, PPARγ2, CIDEA, LPL, ADIPOQ, PGC1α, CEBPA and AP2. The functionality may be assessed by evaluating the mitochondria content, oxygen consumption, or uncoupled-dependent respiration as detailed in the experimental section.

In a second aspect, the present invention also relates to a population of brown/beige adipocytes obtainable or obtained by the method of the invention as described above. Preferably, said population is a population of human brown/beige adipocytes, more preferably a population of adult human brown/beige adipocytes. Preferably, this population is a substantially pure homogenous population, preferably comprising at least 70, 75, 80, 85, 90, 9, 98 or 99% of brown/beige adipocytes.

The present invention also relates to a population of brown/beige adipocytes of the invention for use in cell-based therapy, and in particular for use in the treatment of obesity and/or obesity-related diseases.

In particular, the population of brown/beige adipocytes may be comprised in a 3D culture matrix and/or may be in the form of organoids as described above.

Preferably, the population of brown/beige adipocytes of the invention comprises unilocular adipocytes.

All embodiment described for the method of producing brown/beige adipocytes are also encompassed in this aspect.

In another aspect, the present invention also relates to a method of producing adipogenic progenitors cells comprising contacting cells selected from white adipose tissue cells and mesenchymal stem cells, with a differentiation medium comprising, or consisting essentially of, serum, a glucocorticoid, and a mix of growth factors comprising a growth factor of the VEGF family, a growth factor of the EGF family, an insulin-like growth factor and a growth factor of the FGF family, and optionally a free-radical scavenger or anti-oxidant, until obtaining adipogenic progenitor cells, and optionally recovering said adipogenic progenitor cells. Adipogenic progenitor cells may thus be used in screening methods, for therapeutic purposes or may be further differentiated in brown/beige adipocytes as described above. All embodiment described for the method of producing brown/beige adipocytes are also encompassed in this aspect. In particular, adipogenic progenitor cells may be produced in a 3D culture system and may be in the form of spheroids.

In another aspect, the present invention also relates to a population of adipogenic progenitor cells obtainable or obtained by the method of the invention as described above. Preferably, said population is a population of human adipogenic progenitor cells, more preferably a population of adult human adipogenic progenitor cells. Preferably, this population is a substantially pure homogenous population, preferably comprising at least 70, 75, 80, 85, 90, 9, 98 or 99% of adipogenic progenitor cells. In particular, adipogenic progenitor cells may be produced in a 3D culture system and may be in the form of spheroids.

The present invention also relates to a population of adipogenic progenitor cells of the invention for use in cell-based therapy, and in particular for use in the treatment of obesity and/or obesity-related diseases.

All embodiment described for the method of producing brown/beige adipocytes or the method of producing adipogenic progenitor cells are also encompassed in this aspect.

In a further aspect, the present invention relates to a pharmaceutical composition comprising a population of brown/beige adipocytes of the invention and/or a population of adipogenic progenitor cells of the invention.

The pharmaceutical composition is formulated in a pharmaceutically acceptable carrier according to the route of administration.

Preferably, the pharmaceutical composition is formulated in order to be suitable for use in a cell based therapy in a subject in need thereof.

The pharmaceutical composition may be formulated in accordance with standard pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art.

Preferably, the pharmaceutical composition is suitable for parenteral administration, in particular for intradermal administration or directly into adipose tissue.

Pharmaceutical compositions suitable for such administration may comprise brown/beige adipocytes cells and/or adipogenic progenitor cells, in combination with one or more pharmaceutically acceptable sterile isotonic aqueous or nonaqueous solutions (e.g., balanced salt solution (BSS)), dispersions, suspensions or emulsions, or sterile powders which may be reconstituted into sterile injectable solutions or dispersions just prior to use, which may contain antioxidants, buffers, bacteriostats, solutes or suspending or thickening agents.

Optionally, the composition comprising cells may be frozen for storage at any temperature appropriate for storage of the cells. For example, the cells may be frozen at about −20° C., −80° C. or any other appropriate temperature. Cryogenically frozen cells may be stored in 30 appropriate containers and prepared for storage to reduce rick of cell damage and maximize the likelihood that the cells will survive thawing. Alternatively, the cells may also be maintained at room temperature of refrigerated, e.g. at about 4° C.

The amount of cells to be administered may be determined by standard procedure well known by those of ordinary skill in the art. Physiological data of the patient (e.g. age, size, and weight) and type and severity of the disease being treated have to be taken into account to determine the appropriate dosage.

The pharmaceutical composition of the invention may be administered as a single dose or in multiple doses. Each unit dosage may contain, for example, from 0.1 to 5 /mL of brown/beige adipocytes and /or from 0.1 to 5 /mL of adipogenic progenitor cells.

The pharmaceutical composition of the invention may further comprise additional active compounds such as anti-inflammatory agents, anti-apoptotic agents, immunosuppressive or immunomodulatory agents, antioxidants, growth factors, and/or drugs.

Preferably, in the pharmaceutical composition of the invention, adipogenic progenitor cells are in the form of spheroids as described above. Preferably, in the pharmaceutical composition of the invention brown/beige adipocytes are comprised in a 3D culture matrix and/or are in the form of organoids as described above.

The present invention also relates to a pharmaceutical composition of the invention for use in a cell-based therapy in a subject in need thereof. The present invention also relates to a method for treating a subject suffering from obesity and/or obesity-associated disease, comprising administering to said subject a therapeutically efficient amount of a pharmaceutical composition of the invention, preferably a pharmaceutical composition comprising brown/beige adipocytes.

As used herein, the term "subject" refers to an animal, preferably a mammal, and even more preferably a human, including adult, child and human at the prenatal stage.

The term "obesity" refers to a medical condition in which excess body fat has accumulated to the extent that it may have a negative effect on health, leading to reduced life expectancy and/or increased health problems. A subject is considered obese when its body mass index (BMI), i.e. a measurement obtained by dividing a person's weight by the square of the person's height, exceeds 30 kg/m$^2$.

As used herein, the term "obesity-associated disease" refers to diseases or disorders that have an increased likelihood to appear in obese subjects or are directly caused by obesity. In particular, this term may refer to type 2 diabetes, impaired glucose tolerance, insulin resistance, dyslipidemia, hypertension and cardiovascular diseases.

As used herein, the term "treatment", "treat" or "treating" refers to any act intended to ameliorate the health status of patients such as therapy, prevention, prophylaxis and retardation of the disease. In certain embodiments, such term refers to the amelioration or eradication of a disease or symptoms associated with a disease. In other embodiments, this term refers to minimizing the spread or worsening of the disease resulting from the administration of one or more therapeutic agents to a subject with such a disease.

In particular, the term "treatment of obesity or obesity-related disease" may refer to an increase of fat consumption, a loss of weight, a decrease of the insulin resistance and an improved glycemia.

By a "therapeutically efficient amount" is intended an amount of brown/beige adipocytes and/or adipogenic progenitor cells administered to a subject that is sufficient to constitute a treatment as defined above.

In the method of the invention, the pharmaceutical composition or cells of the invention are preferably administered parenterally, more preferably subcutaneously or directly into adipose tissue.

The cells can be washed (e. g., in isotonic PBS) before implantation to remove any contaminants, including adipogenic agents or components of the growth media, before implantation. The number of required cells is variable and depends on a variety of factors, including but not limited to, the site of implantation, the age, surface area, and clinical condition of the subject. In a particular embodiment, the method comprises the administration of at least 1×10$^6$ brown/beige adipocytes or adipogenic progenitor cells. The administration can be repeated until to obtain a sufficient quantity of brown/beige adipocytes or adipogenic progenitor cells to provide a therapeutic effect.

In a preferred embodiment, brown/beige adipocytes or adipogenic progenitor cells are obtained by the method of the invention from a sample of WAT cells or MSC of the subject to be treated. Thus, in this embodiment, the method may comprise providing WAT cells or MSC from the subject to be treated, obtaining beige/brown adipocytes or adipogenic progenitor cells according to the method of the invention, recovering said beige/brown adipocytes or adipogenic progenitor cells, and administering beige/brown adipocytes or adipogenic progenitor cells to the subject. Alternatively, WAT cells or MSC may be obtained from another subject, preferably from another subject of the same species, i.e. allogenic. In this case, immune suppressor may be administered to prevent rejection of the cells.

The present invention also relates to a method of promoting brown adipogenesis and/or decreasing fat stores or weight in a subject, the method comprising administering to the subject a population of brown/beige adipocytes of the invention or a pharmaceutical composition of the invention comprising brown/beige adipocytes.

The present invention also relates to a kit for the generation of brown/beige adipocytes. The kit may include a differentiation medium as defined above and one or more adipogenic agents, and optionally one or several culture flasks. The kit may further comprise a population of adipogenic progenitor cells of the invention, preferably a population of human adipogenic progenitor cells. Optionally, the kit may further comprise a 3D culture system such as ultra-low attachment plate(s), agarose-coated well plate(s) and/or 3D culture matrix. Preferably, the kit comprises one or several ultra-low attachment plates and a 3D culture matrix. The kit may also further comprise a device for administering cells to a subject, e.g. a syringe, and/or instructions for administration.

The present invention also relates to the use of a kit according to the invention to produce brown/beige adipocytes according to the method of the invention.

The present invention also relates to a method of screening compounds stimulating or inhibiting the shifting of white adipocytes to brown/beige adipocytes, comprising contacting cells selected from white adipose tissue cells and mesenchymal stem cells, with a differentiation medium comprising, or consisting essentially of, serum, a glucocorticoid, and a mix of growth factors comprising a growth factor of the VEGF family, a growth factor of the EGF family, an insulin-like growth factor and a growth factor of the FGF family, and optionally a free-radical scavenger or anti-oxidant, until obtaining adipogenic progenitor cells, contacting said adipogenic progenitor cells with a candidate compound, and assessing the obtaining of brown/beige adipocytes, wherein the candidate compound stimulates the shifting of white adipocytes to brown/beige adipocytes if brown/beige adipocytes are obtained, and alternatively wherein the candidate compound inhibits the shifting of white adipocytes to brown/beige adipocytes if the number of expected brown/beige adipocytes decreases.

The presence of brown/beige adipocytes may be assessed by any method known by the skilled person, in particular by any method disclosed above.

In a particular embodiment, the steps of contacting cells selected from white adipose tissue cells and mesenchymal stem cells, with a differentiation medium and of contacting adipogenic progenitor cells with a candidate compound are performed in 3D culture system as described above.

The candidate compound may be any chemical or biological compound. Candidate compounds stimulating the shifting of white adipocytes to brown/beige adipocytes may be selected as useful drugs for treating obesity or obesity-related disease.

Candidate compound inhibiting the shifting of white adipocytes to brown/beige adipocytes may be selected to be suppressed for treating obesity or obesity-related disease.

The present invention also relates to a method of identifying compounds capable of increasing an activity of the brown/beige adipocytes, in particular modulating the thermogenic program of said adipocytes, comprising contacting a population of brown/beige adipocytes of the invention with a candidate compound; and monitoring the effect of said candidate compound on the activity of brown/beige adipocytes.

The activity of brown/beige adipocytes may be assessed by quantifying one or more molecular markers, assessing mitochondrial biogenesis, oxygen consumption, uncoupled respiration, glucose uptake, lipolysis, fuel metabolism or any other parameter which indicates increased metabolic activity and/or heat generation from brown/beige adipocytes.

Candidate compounds capable of increasing or decreasing an activity of brown/beige adipocytes, such as modulating the thermogenic program of brown/beige adipocytes, are selected. These selected compounds may be of interest for the treatment of obesity and/or obesity-related diseases.

All references cited herein, including journal articles or abstracts, published patent applications, issued patents or any other references, are entirely incorporated by reference herein, including all data, tables, figures and text presented in the cited references.

Although having distinct meanings, the terms "comprising", "having", "containing' and "consisting of" may be replaced with one another throughout the above description of the invention.

In the frame of the present description, all molecules and cells may optionally be isolated and/or purified.

Further aspects and advantages of the present invention will be described in the following examples, which should be regarded as illustrative and not limiting.

EXAMPLES

Example 1

Materials and Methods

ASC Isolation and Expansion

After inform consents, human adipose tissue-derived cells were obtained from 23 healthy donors male and females (median age: 42, range: 34-63; median BMI: 26.95, range: 23.3-32.7; gender distribution 95.5% female, 4.5% male) undergoing elective procedures of abdominal dermolipectomy in the plastic surgery department of Rangueil Hospital (Toulouse, France). 10 g of fresh tissue were minced with scissors in 33 mL of digestion buffer: α MEM (Invitrogen, France) mixed with 1.36 U/mL Collagenase NB4 (Serva Nordmark). After shaking in a warmth bath (37° C., 45 min, 120 rpm), the collagenase activity was stopped by adding αMEM+human Albumin (HSA) 0.1% (v/v) (LFFB, France), tissue was passed through a cell strainer 100 μm (BD Falcon, France) and then centrifuged at 600 g. The supernatant, containing mature adipocytes, was discarded. The pellet identified as the stromal vascular fraction (SVF) was resuspended in 10 mL αMEM+HSA 0.1% and cells were counted with a Malassez hemocytometer. Non-adherent cells were removed after overnight incubation, and the media were changed every 3 days. Then cells were harvested after 8 days of culture by Trypsin (0.05%) (Invitrogen)/EDTA (Ethylendiamine tetra acid) method. This initial passage of the primary cell culture was referred to as passage 0 (P0). Cells were plated for cell culture or for multipotential assessment at a cell density of 2000 and 20 000 cells/cm$^2$ respectively. The population doubling level was calculated by using the following formula: PDL=Ln (Final number of cells/ initial number of cells)/Ln$_2$. The culture media used for cell culture were 1) EGM2 medium (PromoCell GmbH, Heidelberg, Germany), 2) minimum essential medium (αMEM) supplemented with 10% fetal Fetal Bovine Serum (FBS) (StemCellTechnologies, Vancouver, BC, Canada) and 1% penicillin/streptomycin (Invitrogen, Paisley, UK) plus or minus 1 ng/mL recombinant human Fibroblast Growth Factor 2 (rhFGF2) or 3) αMEM supplemented with 2% Platelet Lysate-enriched Plasma (PLP), injectable heparin (1 U/mL) and Ciprofloxacine (10 μg/mL).

Colony Forming Unit-Fibroblast (CFU-F) Assays

For precise CFU-F frequency determination, the method used was limited dilution assay with the assumption that the number of progenitor cells follows a Poisson distribution. Cells from SVF were serially diluted from 128 to 1 cell/well and 12 wells per dilution in 96 wells. The 96-well plates were then incubated at 37° C., 5% CO2, for 10 days. At that time, the plate was rinsed with PBS, fixed in absolute methanol, stained for with Giemsa 10% (10 min), and rinsed with water. The number of negative wells (i.e., those that did not contain colonies of <10 Giemsa-positive cells) was determined for each cell concentration. These data were used to determine the number of CFU-F based on the Poisson distribution according to the equations $F_0=e^{-u}$ and $u=-\ln F_0$ where $F_0$ is the fraction of wells without colonies (negatively staining wells) and u is the average number of precursors or CFU-Fs per well. By solving the equation for the circumstance where the value of u=1 (or a single CFU-F unit per well), the fraction of negatively staining wells is determined as $F_0=37\%$. Thus, under the limit dilution concentration conditions, when three out of eight or 37% of the wells do not contain a colony based on histochemical staining, the number of SVF cells necessary to obtain a single colony was determined. CFU-F frequency is the inverse of this number.

Flow Cytometry

Flow cytometry was performed at P0 on ASCs after 8 days of cultures. Cells were analyzed for expression of specific surface markers characterizing specific type of cells: hematopoietic, native and cultured mesenchymal stem cells, culture ASC and osteoblastic cells. Briefly, approximately $5*10^4$-$2*10^5$ ASCs were used for CD45-PE;-VioBlue, CD31-PE;-FITC, CD90-PE, CD73-PE;-eFluor710, CD34-PE;-ECD, CD13-PE, CD271-PE;-APC, SSEA3-FITC, SSEA4-PE, CD146-FITC;-PE, CD235a-APC750 markers and ALPL-PE (alkalin phosphatase liver) antibodies. These cells were blocked by Flow cytometry solution (0.1% HSA+ PBS; phosphate buffered solution), and incubated with different antibodies conjugated to different fluorochromes, and then passed through flow cytometer (Beckman, ADP Cyan cytometer). Dead cells were excluded for analysis by DAPI staining. Data were processed by Kaluza version 1.2 Software (Beckman Coulter®).

DNA Chips Analysis

Amplification of mRNAs for Gene Expression Analysis cDNA synthesis and amplification were performed on high quality RNA (RQI>9.8) by the Ovation® PicoSL WTA System V2 protocol (NuGEN®) known to be a robust and sensitive method which utilizes a linear, isothermal amplification of only original transcripts. For first strand cDNA synthesis, 25 ng RNA was utilized with a primer mix containing both poly T sequences and random sequences for whole transcriptome coverage. PolyA RNA controls (GeneChip Poly-A RNA Control kit) containing Poly-A RNA spikes were introduced in the reaction at final control at the final ratio of copy number (Lys 1:100.000; Phe 1:50.000; Thr 1:25.000; dap 1:6.667). Following second strand synthesis, the second cDNA strand was used as template for amplification of single-stranded antisense cDNA products homologous to the first strand cDNA utilizing the Ribo-SPIA™ technology. For detailed methods, please see the manufactory protocols (see Worldwide web site: nugeninc.com/nugen/index.cfm/support/user-guides/). The amplified SPIA cDNA was further purified with the use of Agencourt®RNAClean XP Kit (Beckman Coulter Genomics, Cat #A63987) on a magnetic plate. The purified amplified cDNA samples were dosed by Nanodrop, then 2.5 μg of amplified cDNA were fragmented and biotinylated using the Encore™ Biotin Module (NuGEN®).

Hybridization and Data Processing

Amplified, fragmented and biotin-labeled cDNA targets were prepared with GeneAtlas Hybridization, wash and stain kit for WT array strips and GeneChip Hybridization Control Kit (20X eukaryotic hybridization controls and control oligonucleotide B2) according to manufacturer's protocol. The solutions were hybridized (48° C., 20 h) to Affymetrix® HuGene1.1STArray Strip Kit (Affymetrix®, Santa Clara, Calif.), then washed and stained on a GeneAtlas™ System according to the Affymetrix GeneChip® Expression Analysis Technical Manual (P/N 08-0306 Rev. A). Each samples from same donor were hybridized together to impair potential hybridization batch bias. The arrays were scanned using the Affymetrix GeneAtlas imaging station. The scanned images (DAT files) were processed using the AGCC (Affymetrix GeneChip Command Console) software, and CEL files were imported into Partek® Genomics Suite™ software (Partek, Inc. MO, USA). The Robust Multichip Analysis (RMA) algorithm was applied for generation of signal values and normalization. On each array 36.079 total RefSeq transcripts could be detected. Principal component analysis was performed for global 3D unsupervised analysis. Supervised analysis for generation of each specific gene expression signatures was performed by Partek® Genomics Suite™ software using the sample-paired t-test that matches each donor and treatment. Gene Expression Signature was carried out for Fold Changes >|2|, p<0.05.

Functional Annotation and Data Mining

Gene Ontology enrichment was carried out by Partek® Genomics Suite™ software. Ingenuity Pathway Analysis (IPA) allowed to Gene networks and canonical pathways representing key genes were identified through the use of Ingenuity Pathway Analysis, IPA (Ingenuity® Systems, "see Worldwide website: ingenuity.com/"). Briefly, the data sets containing gene identifiers and corresponding fold change and p-values were uploaded into the web-delivered application and each gene identifier was mapped to its corresponding gene object in the Ingenuity Pathway Analysis (IPA) software. Fisher's exact test was performed to calculate a p-value assigning probability of enrichment to each biological function and canonical pathway within the IPA library. Obtained PS lists were analyzed by Ingenuity Pathway Analysis (Ingenuity® Systems, see Worldwide website: ingenuity.com) and classified by Gene Ontology subcellular localization and type.

Gene Set Enrichment Analysis (GSEA) (Subramaniana A., PNAS, 2005) software was performed on the median 'signal-to-noise ratio' of EGM2-ASC group to Standard Conditions-ASCs group using the genes sets obtained by home-made in vitro differentiation GEP and curated gene sets from $RT^2$ profilers from Qiagen.

Quantitative RT-PCR

Total RNA was extracted from ASCs and purified by AllPrep DNA/RNA/Protein kit (Qiagen, Courtaboeuf, France) and dosed by nanodrop (Thermo Fischer, Courtaboeuf, France). RNA purity and integrity was checked using the Experion™ RNA Std Sens Reagents on the Experion automatisated system (Biorad). All samples used for cDNA synthesis displayed a RNA integrity number (RIN) above 9.8. The reverse transcription (RT) was performed on 1 μg RNA by using high capacity cDNA reverse transcription kit (Applied Biosystem ™) and random hexamers in a final volume of 20 μL. The oligonucleotides for each target of interest, designed by using Primer Express software (PerkinElmer Life Sciences, Waltham, Mass.) were used (forward and reverse) and listed in table1. Quantitative PCR was performed on diluted cDNA (equivalent to 25 ng of starting purified RNA) using SSoFast EvaGreen Supermix (Biorad, Marnes-la-Coquette, France) with 500 nM of forward and reverse primers in a total volume of 20 μL on a CFX™ Real Time System (Biorad) following: 95° C., 3 minutes and 40 cycles of denaturation (95° C., 10 seconds) and primers hybriation and amplification (60° C., 30 seconds). Each primer couple displayed interpretable PCR efficiencies (95%-105%). Melt curves and appropriate No RT control were used to validate amplification specificity. Data were analysed on Bio-Rad CFX manager (threshold=0.2), exported to DataAssist Software v3.0 (Applied Biosystems). Gene expression was calculated using the $2^{-\Delta Ct}$ (or $2^{-\Delta\Delta Ct}$) method using PPIA as appropriate reference gene which had the lesser M score. All real-time PCR reactions for the individual samples were performed in duplicate.

Western Blot Analysis

Proteins which were extracted by AllPrep DNA/RNA/Protein kit (Qiagen, Courtaboeuf, France) were subjected to the Western blot analysis. Briefly, eluate from DNA and RNA retention columns was precipitated by APP buffer (v/v), centrifuged (10,000 g, 10 min), washed by ethanol 70%, and air dried. Pellets were dissolved in ALO buffer (Qiagen, Courtaboeuf, France), sonicated and protein content was determined by Bicinchoninic Acid method (Pierce). After denaturation (95° C., 5 min), proteins were separated by 12% Tris-glycine-SDS polyacrylamide gel electrophoresis, and subsequently transferred to polyvinylidene difluoride membrane (PVDF). The proteins were detected with Rabbit polyclonal Ab anti-human SOX2 (ab97959; Abcam, Cambridge, UK), anti-human OCT4 (ab19857, Abcam), anti-human NANOG (SC33759; SantaCruz, Dallas, Tex.), anti-human PRDM16, anti-human UCP1, or with Mouse monoclonal Ab anti-human PPARG, anti-βActin and anti-RUNX2 (Abcam) antibodies. Immuno-complexes were revealed by a secondary antibody conjugated to Horse Radish Peroxidase and visualized by a molecular imager (Biorad, Chemi Doc ™). The βactin was used as internal positive control (Sigma).

Electro Mobility Shift Assay (EMSA)

Cells grown in each medium were detached by Trypsine/EDTA method, counted on a hemocytometer, washed in ice-cold PBS and processed to separation of nuclear and cytoplasmic protein fractions thanks to the NE-PER Nuclear and Cytoplasmic extraction reagents (Pierce-ThermoScientific) according the manufacturer's instructions. Protein contents were dosed by BCA method. EMSA was performed using LightShift Chemiluminescent Kit (Pierce-ThermoScientific). Conditions and probe sequences were adapted from Rodda David J et al, JBC 2005. Briefly, nuclear extracts (5 μg) were incubated (RT, 20 min) with 1 femtomol double strand DNA oligonucleotides (Eurogentec, Liege, Belgium) were 5' end of sense oligonucleotide is Biotynilated in a reaction buffer (1× binding buffer, 10 ng/mL Poly dIdC, 6% Gycerol, 60 mM KCL, 1mM EDTA). Competition was performed by adding 2 picomol of unlabeled double strand. DNA/protein mixes were loaded with 5× loading buffer on a non-denaturating polyacrylamide gel (6% in TBE 0.5×). The end of the procedure was performed according manufacturer's instructions and chemiluminescence was visualized by a molecular imager (Biorad, Chemi Doc ™).

Multipotential Capacity Tests

Adipocytic Differentiation

For adipocyte induction, two distinct media were used: the first was composed of αMEM with 10% FBS, 1 μM dexamethasone, 0.45 mM isobutylmethylxanthine (IBMX), 60 μM Indomethacin and 1% penicillin/streptomycin (Sigma) for phenotypic analysis and the second was composed of αMEM with 10% FBS, 5 μg/mL insulin (Sigma), 60 μM Indomethacin, 1 μM Dexamethasone and 1 μM Rosiglitazone. Cells were maintained in culture for up to 7 or 10 days, with the media replaced every 3 days. Cultures were rinsed with PBS and fixed in glutaraldehyde 3% (room temperature, 45 min) and adipocyte differentiation was determined by staining of neutral lipids with oil red O. The percentage of absorbed oil red for each medium was performed by solving the oil red in isopropanol and measuring the dosage in 510 nm spectrophotometer (VARIOSSKAN, Thermo). In some experiments, confluent ASC were stimulated 3 days by 50 ng/mL of either rhBMP4 (Bone Morphogenetic Protein 4, Miltenyi, Bergen Gladbach, Germany) or rhBMP7 (RnD system's) in αMEM, 2% FBS.

Osteoblastic Differentiation

Confluent cultures of cells were induced to undergo osteoblastic fate by adding 50 μM Ascorbic acid, 10 mM β-glyserophosphate (Sigma Aldrich, Lyon, France), in basal medium composed of αMEM , 2% FBS, 1% L-Glutamine. Cultures were replaced by fresh osteogenic medium every 3 days. At day 11 and 17, cultures were rinsed in PBS and fixed by 4% formaldehyde, and osteogenic differentiation was determined by revealing the calcium phosphate deposition with Alizarin red. The percentage of absorbed red alizarin for each medium was performed by solving the red alizarin in acetic acid 10% and measuring the dosage in 405 nm with a correction on 600 nm in spectrophotometer (VARIOSSKAN, Thermo, France).

Chondrogenic Differentiation

Confluent cultures of ASCs in P1 were induced to undergo chondrogenesis by replacing the stromal medium with chondrogenic induction medium composed of DMEM high glucose complemented by 1 mM Sodium pyruvate, 0.1 μM dexamethasone, 0.17 mM Ascorbic-2-phosphate acid, 0.35 mM L-Proline, 1% ITS+1(Insulin Transferin selenium) (Sigma-Aldrich). TGFβ3 (Transforming Growth Factor 3) was added in the concentration of 10 ng/mL. Cultures were replaced with fresh chondrogenic induction medium every 3 days for a period of up to 3 weeks. Cultures were washed with PBS and fixed by Paraformaldehyde 10% and stained by the Alcian blue for glycosaminoglycans.

$O_2$ Consumption

The whole cell layer of differentiated adipocytes was harvested and incubated in culture medium without serum and supplemented with 4% free fatty acid BSA in a magnetically stirred oxygen electrode chamber thermostated to 37° C. Oxygen consumption was measured polarographically using a Clark oxygen electrode (Oxygraph-2K Oroboros). The chamber was closed and the cells were incubated to determine the basal respiratory rate. Oligomycin (2 μg/ml) was then added to measure the coupled respiration rate and antimycin (20 μM) to measure mitochondrial-derived oxygen consumption. Oxygen consumption rate was determined from the slope of a plot of O2 concentration versus time.

Immuno-Fluorescence

After expansion, ASC- or EGM-2-derived cells were also cultured in chamber slides and after becoming confluent, cells were induced to differentiate into brown/beige adipocytes. After 7 days, the cells were stained with anti-UCP1 antibody (Alpha Diagnostic, San-Antonio, Tex.), and then with Alexa488-labeled goat anti-mouse secondary antibody (Invitrogen). The staining was read by using confocal microscope (Zeiss 510, Zeiss, Oberkochen, Germany).

Statistical Analysis

Statistical analyses were performed on GraphPad PRISM 5 software with the nonparametric Wilcoxon matched paired test. Stars indicates the statistical significance between 2 conditions (*: P<.05; : P<.01;*: P<.001).

Results

Adult human white adipose tissue cells were cultured in an EGM2 medium which has been previously designed to retain perivascular stem/progenitor cells. Simultaneously, as controls, adult human white adipose tissue cells were also cultured in standard conditions, i.e. medium containing 10%

(v/v) FBS with 1 ng/mL FGF2 or medium containing 2% plasma-derived platelet lysate (PLP).

Figure 2:
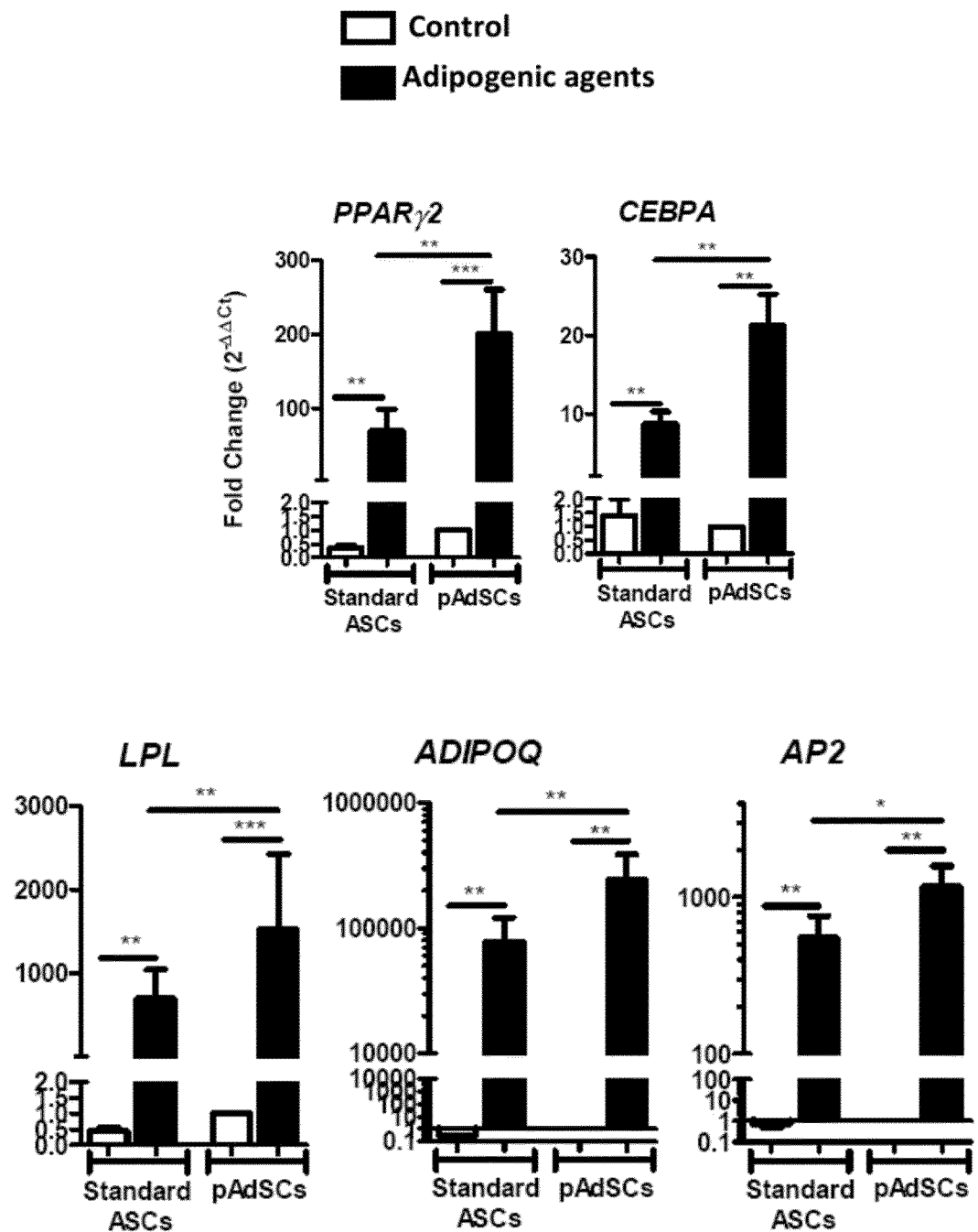
FIG. 2: pAdSCs promptly differentiate into adipocytes when treated with pharmacological adipogenic agents. Adipogenic pharmacologic agents were used to induce adipocyte differentiation. These adipocyte agents were: rosiglitazone (a thiazolidinedione family PPARγ activator), insulin, dexamethasone and indomethacin. At day 7 post-induction, mRNAs were extracted from cultured cells and QRT-PCR was performed. Expression of adipocyte markers were studied notably PPARγ2, CEBPA, LPL, ADIPOQ and AP2. Data are depicted as relative expression (2-ddCt method) compared to housekeeping gene PPIA as reference transcript. Non-parametric paired Wilcoxon test was used to compare the mean differences. *p<0.05; p<0.001; *p<0.001.

Adherent cells cultured in EGM2 medium gave rise to highly proliferating colonies consisting in highly immature perivascular stem/progenitor cells capable to generate several types of differentiated cells (FIG. 1). In some aspects, the phenotype of these EGM2-derived cells was resembling adipose-derived stromal cells from standard controls (thereafter referred to as standard ASCs) (FIG. 1A). However, surprisingly, EGM2-derived cells were shown to be very immature compared to standard ASCs. Indeed, EGM2-derived cells were found to be strongly positive for the stemness factors NANOG, OCT4 and SOX2 (FIG. 1B) and to express very low level of several lineage markers notably those of osteoblastic (RUNX2, DLX5, ALPL), chondroblastic (not shown) and smooth muscle cell (ACTA2, CNN1, CNN3, TAGLN) lineages (FIG. 1C). On the opposite, standard ASCs expressed at a larger extent osteoblastic, chondroblastic and vascular smooth muscle lineage markers and were barely positive for stemness factors (FIG. 1B and C). Depending to molecular inducers, these EGM2-derived cells were able to differentiate into osteoblastic, chondroblastic and adipocytes (FIG. 1D). Interestingly, ASCs were more potent to give rise to osteoblasts and chondroblasts whereas EGM2-derived cells (thereafter referred to as adipogenic progenitor cells) were more prone to form adipocytes (FIG. 1D). Accordingly, after treatment with different adipogenic agents (insulin, dexamethasone, indomethacin, rosiglitazone), adipogenic progenitor cells expressed higher levels of adipogenic genes such as PPARγ2, CEBPA, LPL, ADIPOQ, and AP2 compared to standard ASCs (FIG. 2).

Figure 3:
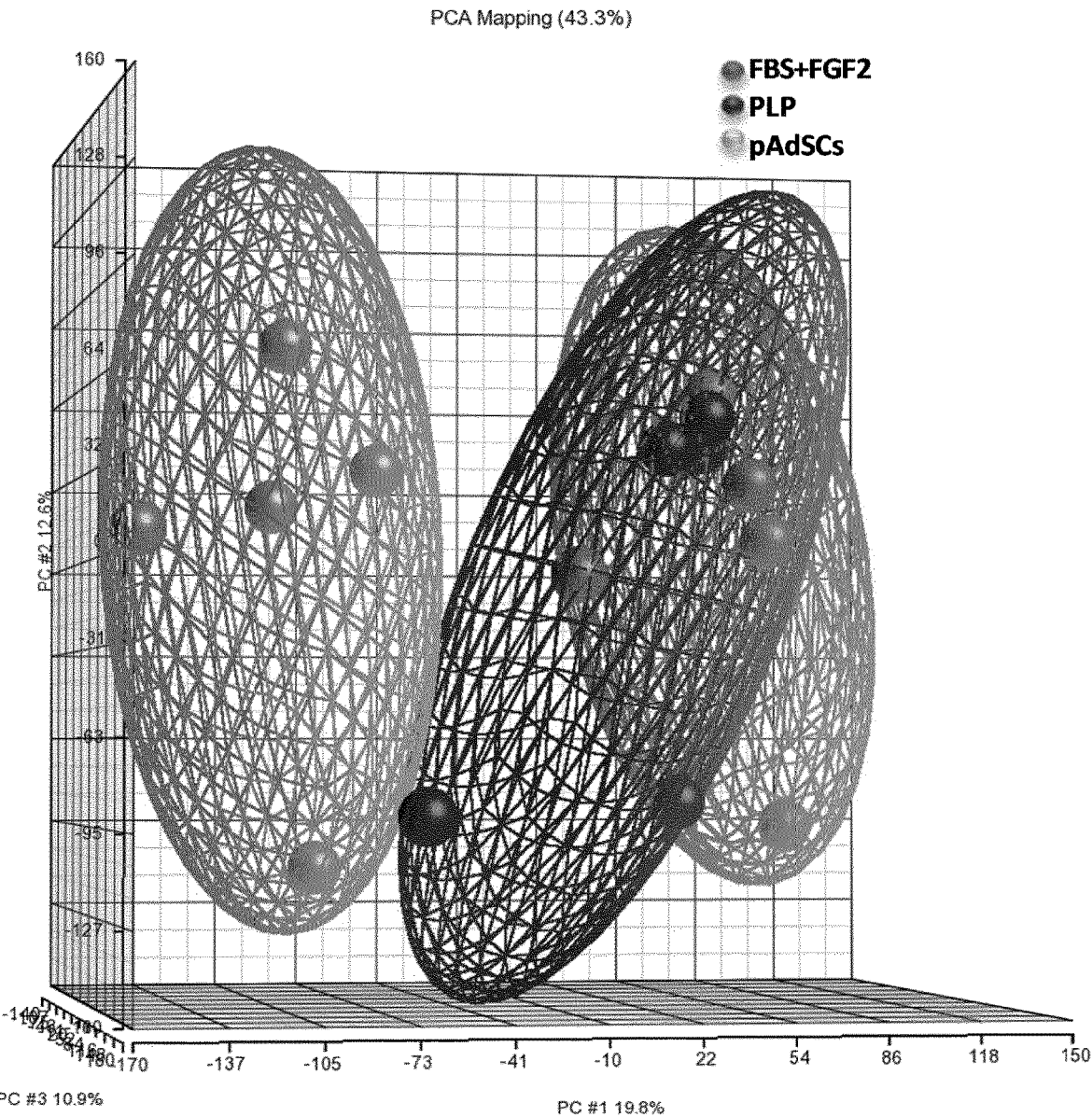
FIG. 3: Gene expression profiling of adipogenic progenitors compared to standard ASCs. Adipogenic progenitor cells and the two types of standard ASCs (PLP and FBS+FGF2-derived ASCs) were subjected for high throughput studies. (A): The principal component analysis (PCA) shows the three populations. Adipogenic progenitors (pAdSCs) are clearly different to the others in term of gene expressions. (B): The number probe sets (PS) that are significantly different between each type of cells.
Figure 3:
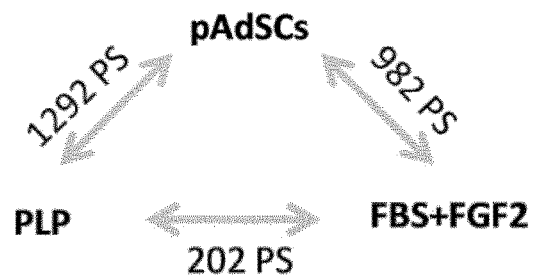

These results suggested that despite a relative similar phenotype between standard ASCs and adipogenic progenitors, some functional properties and phenotypic traits are clearly different. These data prompted the inventors to go more deeply in characterization by performing high throughput studies. Unsupervised analysis determined by Principal Component Analysis (FIG. 3a) showed that adipogenic progenitor group was obviously segregated from the different types of standard ASCs which remained closed. This first steps of bioinformatics analysis of gene expressions demonstrated that adipogenic progenitors were clearly distinct from standard-ASCs. Supervised analysis that determines the gene expression signature between each group (Fold Change>|2|; paired sample t test<0.05) demonstrated the high divergence of adipogenic progenitors compared to standard ASCs, e.g. PLP-ASCs (1292 ProbeSet[PS]) and to 10% FBS+FGF2-ASCs (982PS), while lower changes are noted between PLP-ASCs and 10% FBS+FGF2-ASCs (202PS) (FIG. 3b). In order to generate a "standard ASC vs adipogenic progenitor" gene expression signature, common genes of standard ASCs, comprising those found for PLP-ASCs and 10% FBS+FGF2-ASCs, were compared to adipogenic progenitor signature (Data not shown). Therefore, adipogenic progenitors were obviously distinct to standard ASCs and could be considered as particular population.

Figure 4:
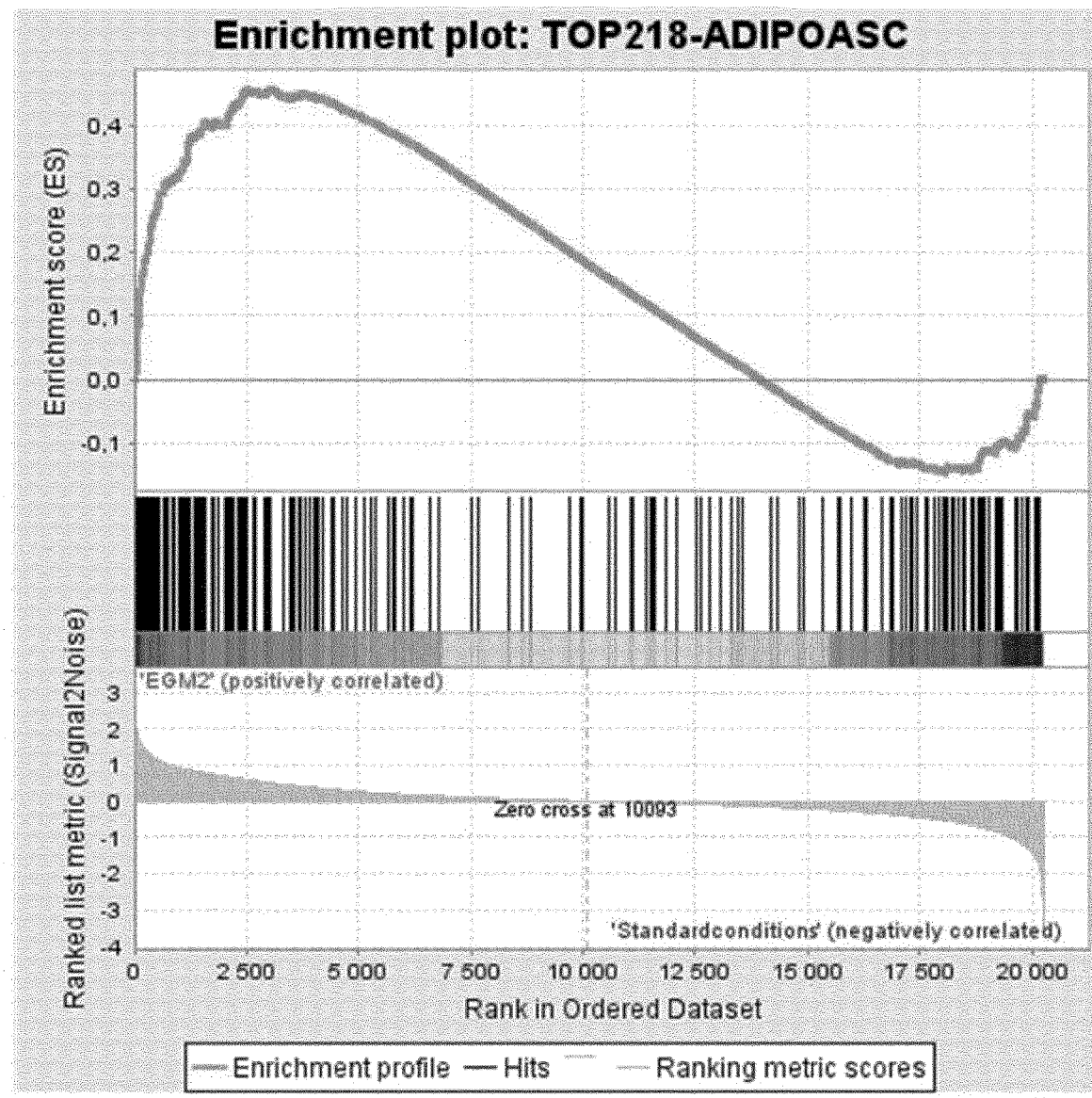
FIG. 4: Adipocytic vs osteoblastic commitment of adipogenic progenitors compared to standard-ASCs. GSEA Enrichment Scores (ES) curves for the Top genes upregulated (left) or downregulated (right) in adipogenic progenitors or in standard ASCs when compared to an adipocytic gene list (A) or osteoblastic gene list (B). FDR q-value is indicated above.
Figure 4B:
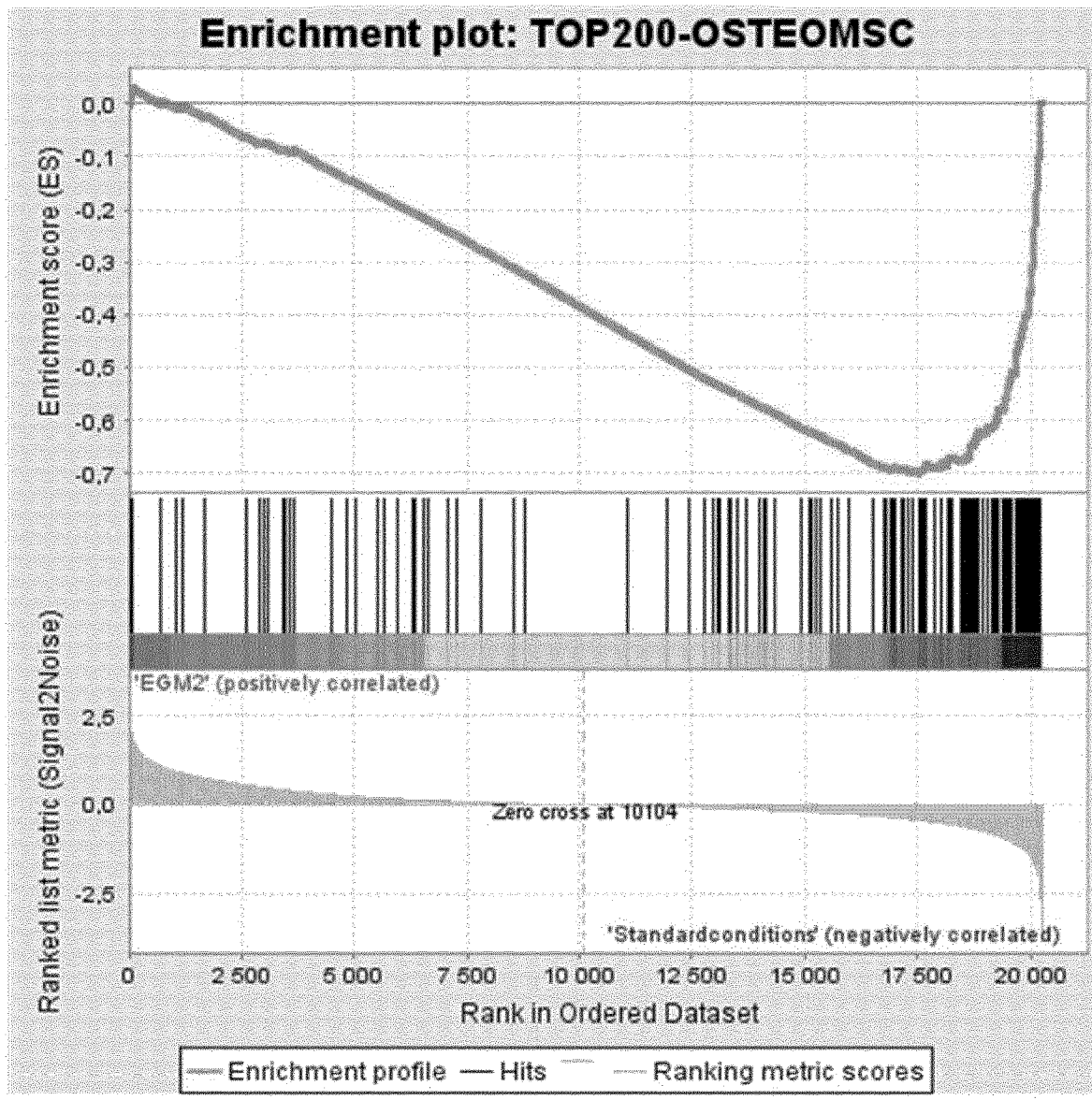

The inventors then sought the main biological pathways and molecular mechanisms that could be characteristic of adipogenic progenitor cells when compared to standard ASCs. Their signatures were analyzed and showed that adipogenic progenitor signature was highly enriched in genes implicated in cell proliferation cellular movement developmental systems and lipid metabolism (Data not shown). These data fitted well with those described above i.e. the proliferation properties of adipogenic progenitors and their differentiation potentials and evidences that they were more prone to get into adipocyte lineage. On the contrary, standard ASCs were shown to exhibit a signature that was enriched in osteoblastic genes as demonstrated by our Gene Set Enrichment Analysis data (FIG. 4). This latter observation suggested us to use other type of differentiation inducers notably Bone Morphogentic Proteins. Indeed, it is well known that BMP4 or BMP7 are osteo-inducers for osteogenic progenitors whereas they induce adipocyte differentiation for adipogenic stem/progenitor cells. Therefore, according to the origin of cells tested, i.e. adipogenic progenitors or standard ASCs, BMPs could have opposite effects in their commitment.

Figure 5:
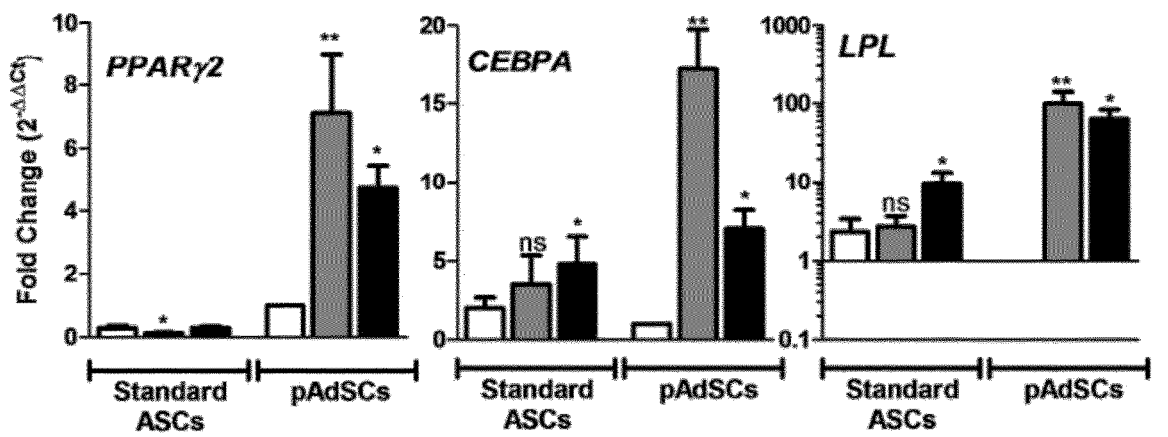
FIG. 5: pAdSCs undergo adipogenic differentiation after BMP induction. Standard ASCs and pAdSCs were stimulated either by vehicle (control), recombinant human rhBMP4 or rhBMP7 for 3 days and recovered at day 10. (A): mRNAs were extracted and QRT-PCR analysis was performed for quantifying key adipocyte markers including PPARy2, CEBPA, LPL, AP2 and ADIPOQ. The white adipocyte specific marker LEP (Leptin) was also evaluated. (B): phase contrast microscopy of Oil red O staining of ASCs and pAdSCs after BMP treatment. (C): Since BMP can also induce osteogenesis, expression of the osteoblastic markers DLXS and OSX were tested. These molecules were significantly more expressed in standard ASCs compared to pAdSCs.
Figure 5:
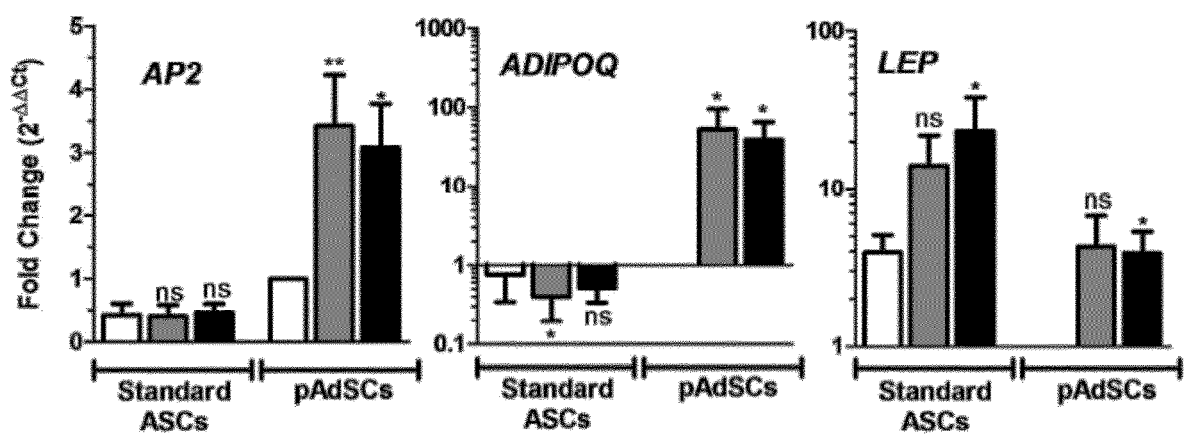

As expected, treatment with either BMP4 or BMP7, induced very different responses in adipogenic progenitor cells compared to standard ASCs. Indeed, in contrast to standard ASCs which expressed high levels of osteoblastic markers when treated with BMP4/7, adipogenic progenitor cells generated clearly defined adipocytes (FIG. 5).

Figure 6:
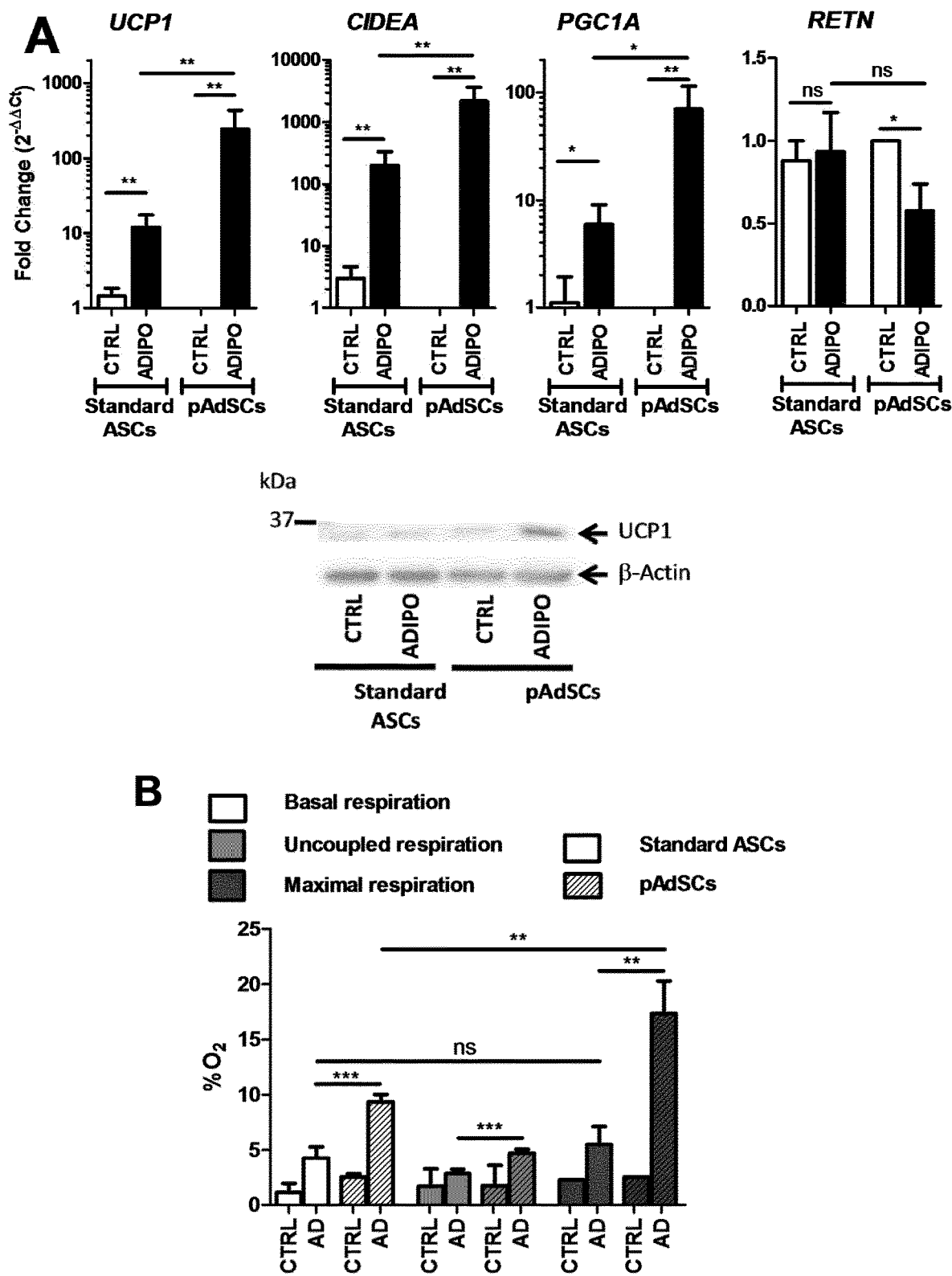
FIG. 6: pAdSCs generate genuine brown/beige adipocytes. Adipogenic agents are used during 7 days to induce adipocyte fate from standard ASCs or pAdSCs. (A): mRNAs and proteins are then extracted for analysing key brown/beige adipocyte markers (by QRT-PCR (UCP1, CIDEA, PGC1A) and western blotting (UCP1)). RETN gene is used as white adipocyte marker. (B): $O_2$ consumption of adipocyte differentiated from standard ASCs or pAdSCs under basal conditions (basal respiration, white boxes) or after CCCP treatments (maximal respiration, black boxes). Non-induced cells are used as control (CTRL). Data are depicted as percentage of $O_2$ consumption, rate of purified rat mitochondria is used as reference. Non-parametric paired Wilcoxon test is used to compare mean differences. p<0.01; *p<0.001. (C): Expressions of brown adipocyte markers were evaluated by Western blot (UCP1), immuno-fluorescence in situ (UCP1) and QRT-PCR (UCP1, CIDEA and PGC1A) at day 3 and 10 after BMP4 or BMP7 induction. PPARγ1 and PPARγ2 were used as adipocyte marker controls and β-actin as internal control. *p<0.05m; **p<0.001; ns: non-significant.

Since BMP4 and more specifically BMP7 are known to be browning agents, the inventors investigated whether these adipocytes had brown/beige phenotype. Data shown in FIG. 6 demonstrated that adipocytes deriving from adipogenic progenitor cells of the invention were genuine brown/beige adipocytes after treatment with an adipogenic agent. The brown/beige adipocytes deriving from adipogenic progenitor cells expressed high PPARγ2, UCP1, CIDEA, LPL, ADIPOQ and AP2 mRNAs levels. The UCP1 was strongly induced at protein level as shown by western blotting and immuno-fluorescence studies. This induction was more potent and reliable upon BMP7 treatment than BMP4. On the opposite, the white adipocyte marker RETN was found to be down-regulated in those cells confirming their browning state. Interestingly, by using BMP4 or BMP7, standard ASCs have preferentially expressed osteoblastic markers (RUNX2 and OSTERIX) (FIG. 5).

Functionally, brown/beige adipocytes were characterized by higher mitochondria content and activity. $O_2$ consumption tests confirmed these results (FIG. 6B). Indeed, differentiated adipogenic progenitor cells displayed near 2 fold more $O_2$ consumption than differentiated standard-ASCs under basal state. The uncoupled-dependent respiration (obtained after oligomycin treatment) was also significantly higher in differentiated adipogenic progenitor cells. Lastly, maximal respiration obtained after CCCP treatment was more than 3 times higher in those differentiated cells. These data were in line with a genuine and functional beige/brown adipocyte state obtained only with adipogenic progenitor cells.

Figure 7:
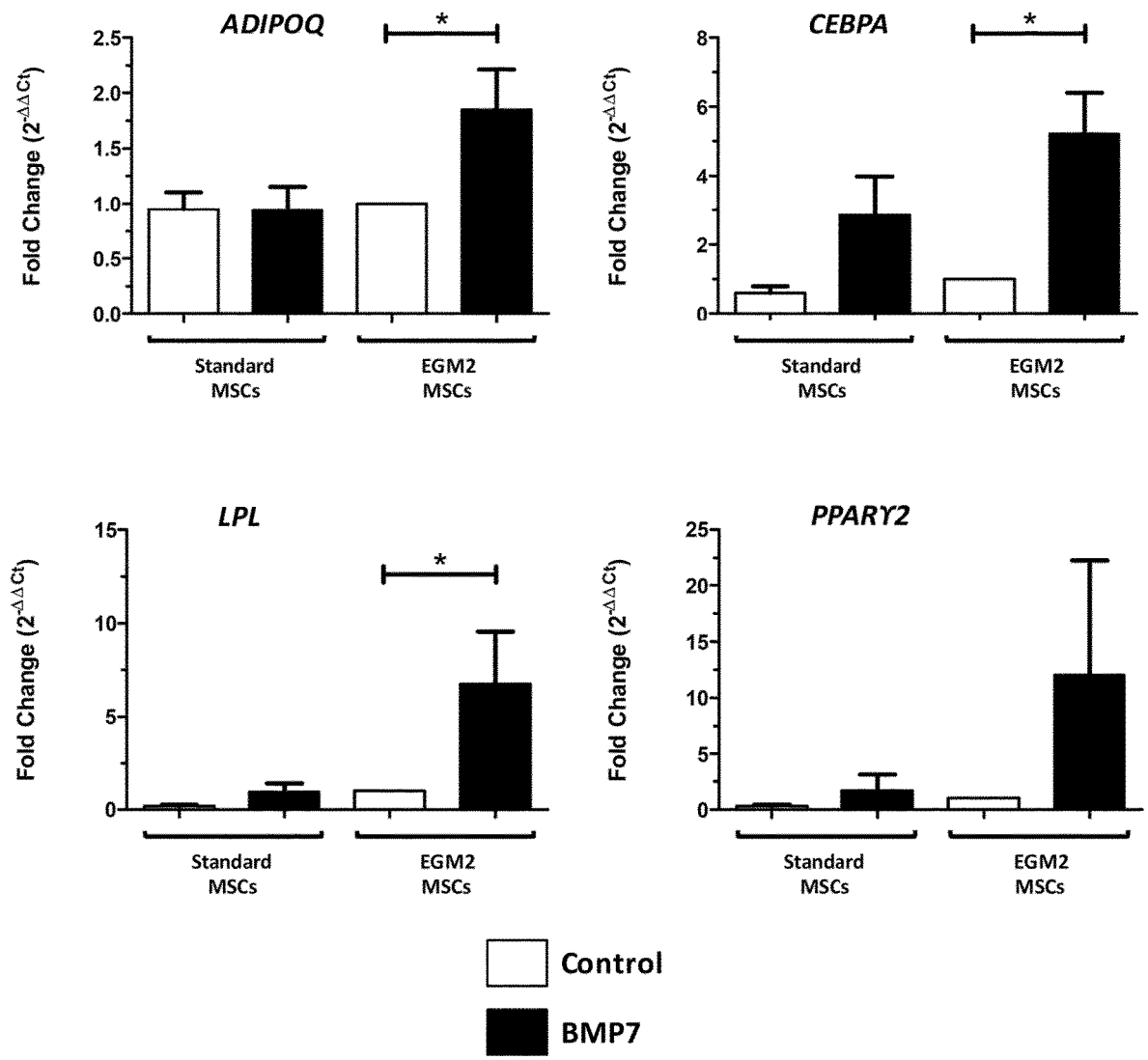
FIG. 7: MSC deriving from EGM2 give rise to brown/beige adipocytes. The pro-beige/brown adipocyte factor BMP7 is used to induce the differentiation of BM-MSCs cultured either in standard medium or in EGM2. (A): mRNAs and proteins are then extracted for analyzing by QRT-PCR adipogenic markers (ADIPOQ, CEBPA, LPL and PPARγ2), (B) key beige/brown adipocyte markers (UCP1, CIDEA) and (C) also osteoblastic markers (OSX and DLX5).

The effect of the method of the invention is not restricted to cells derived from white adipose tissue because when this method was applied on MSC from bone marrow, similar results were obtained. Indeed, BMP7 treatment triggered expressions of adipogenic and UCP1, CIDEA genes in EGM2-derived Bone Marrow-MSCs. In contrast, MSCs cultured in standard conditions were able to differentiate into osteoblastic cells solely (FIG. 7).

Example 2

Materials and Methods
Spheroid Generation and Analyses
Stromal vascular fraction (SVF) from adult human adipose tissue was seeded in 96-wells Ultra-low attachment (ULA) plates at 25 000 cells/well in EGM2 medium. Cells spontaneously aggregated into spheroids within 5-6 days. Spheroids were then transferred into matrigel droplets. To this end, parafilm was layered on an empty tip trail, and small dimples were created by pressing a small spatula on the parafilm. Each dimple was filled with 40 µl matrigel, and the spheroids were transferred to the matrigel droplet using a cut pipet tip. Matrigel droplets were incubated for 45 min at 37° C. until they solidified, transferred to 24-well ULA plates using a spatula and cultured in EGM2 medium for 4 days under agitation (70 rpm) to allow sprouting. Adipocytic differentiation was induced for 10 days under agitation with an adipogenic cocktail containing BMP7 (50 ng/mL), Insulin (5 µg/mL), Apotransferrin (10 µg/mL), and Intralipids (0.2% v/v) in α-MEM medium supplemented with 2% Fetal Bovine Serum. To increase adipocyte browning, Forskolin was added for 4 h at 50 µM.

To compare lipid accumulation in adipocyte droplets in 2 dimensions (2D), SVF was seeded at 75 000 cells/cm2 in standard 24-well plates and cultured in EGM2 medium for 5 days. Adipocyte differentiation was then induced for 10 days by the same adipogenic cocktail used for spheroids. Spheroids or cells in 2D were fixed in 4% paraformaldehyde for 2 h or 20 min, respectively, followed by nuclei staining with DAPI (1/10 000) for 10 min. Image acquisition was performed using a Nikon TE2000-S fluorescence microscope.

For qRT-PCR analyses, 8 spheroids were collected and incubated twice in cold PBS for 15 min to remove matrigel, and then lysed in Qiazol. RNA extraction was performed using the RNeasy micro kit (Qiagen) according to the manufacturer's instructions. Reverse transcription was made with the High Capacity cDNA Reverse Transcription Kit (Applied Biosystems). For qPCR, we used the qPCR Fast SYBR® Master Mix (Applied Biosystems) and the reaction was performed on StepOne™ Plus system (Applied Biosystems).

Spheroid Transplantation and Explant Analyses

Per injection, 30 differentiated spheroids were collected and incubated twice in cold PBS for 15 min to remove matrigel. Meanwhile, a mixture containing one third 1.2% methocel (w/v) (Sigma-Aldrich), one third 10 mg/ml fibrinogen, and one third EGM2 medium (Promocell), supplemented with 1 µ/ml VEGF and FGF-2, was prepared. Spheroids were then resuspended in 200 µl of the methocel/fibrinogen/EGM2 mixture. Just before injection, 3U of thrombin and 200 µl of cold matrigel were added, and the spheroids were injected subcutaneously in the flank of Nude mice using a 19G needle. One week after transplantation, human and mouse vasculature were labeled via retro-orbital injection of human-specific Lectin (Biotinylated Ulex Europaeus Agglutinin I) and mouse-specific Lectin (Rhodamine Griffonia Simplicifolia I). Mice were sacrificed 20 min after injection, and plugs were dissected out and fixed overnight at 4° C. in 4% paraformaldehyde. To visualize human vasculature, whole mount staining was performed with Alexa Fluor 488 streptavidin, followed by nuclei staining with DRAQS.

Results

In order to get closer to physiological relevant conditions, the inventors developed an adipose organoid which mimics the cellular interactions occurring in vivo. To generate this 3D model, adipose tissue-derived SVF was seeded in ULA plates in EGM2 medium to allow spheroid formation. Spheroids were then transferred into matrigel droplets, and differentiated using a physiological adipogenic cocktail containing BMP7, Insulin, Apotransferrin and Intralipids.

Figure 8:
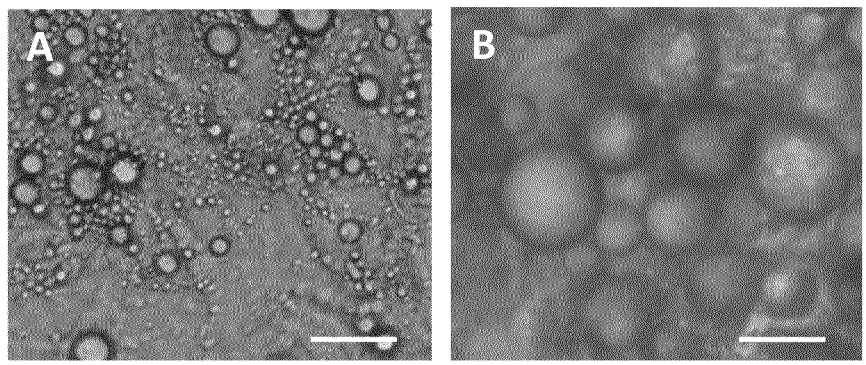
FIG. 8: Adipose organoids express brown/beige markers. (A,B) Representative images of adipocytes generated in a 2D (A) or 3D (B) culture system. Nuclei were labeled with DAPI. Scale bar: 20 μm. (C) Expression of PPARG2, UCP1 and PGC1α was assessed by RT-qPCR in undifferentiated spheroids (control), or after adipocyte differentiation (AD), with or without induction by 50 μM forskolin (fsk) for 4 h.
Figure 8:
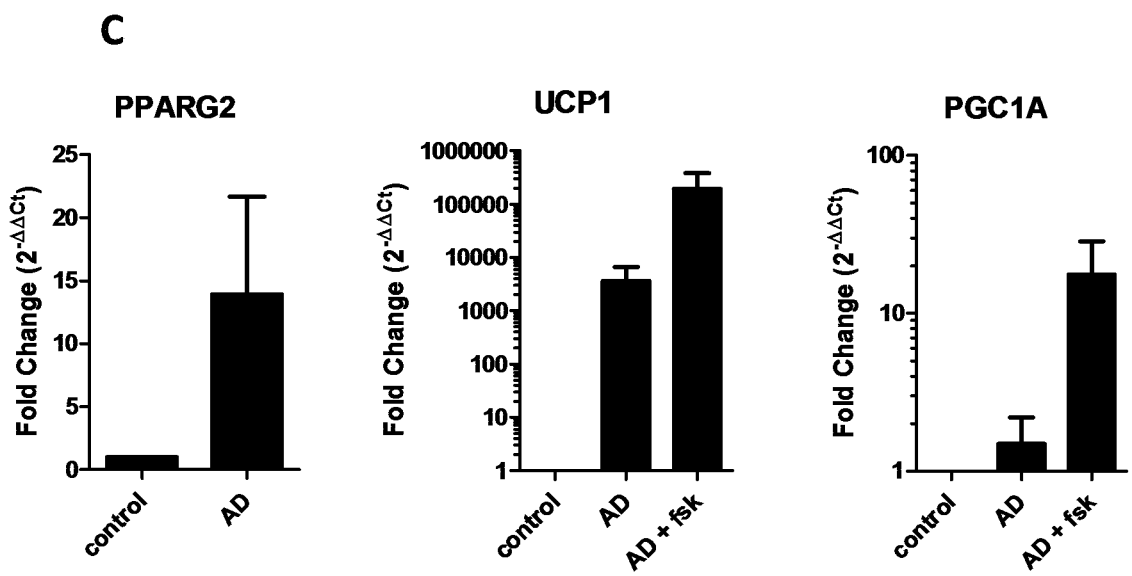

Contrarily to 2D culture, this 3D approach led to the formation of unilocular adipocytes resembling the morphology of mature adipocytes found in vivo (FIG. 8A, 8B). In addition, the inventors observed that endothelial cells were able to self-organize in networks with a tubular morphology and seemed to form lumina, which was not the case in 2D culture. The differentiated spheroids expressed adipocytic markers including PPARG2, as well as the beige/brown markers UCP1 and PGC1A in basal conditions (FIG. 8C). Of note, UCP1 and PGC1A levels were further increased by the browning inducer Forskolin.

Figure 9:
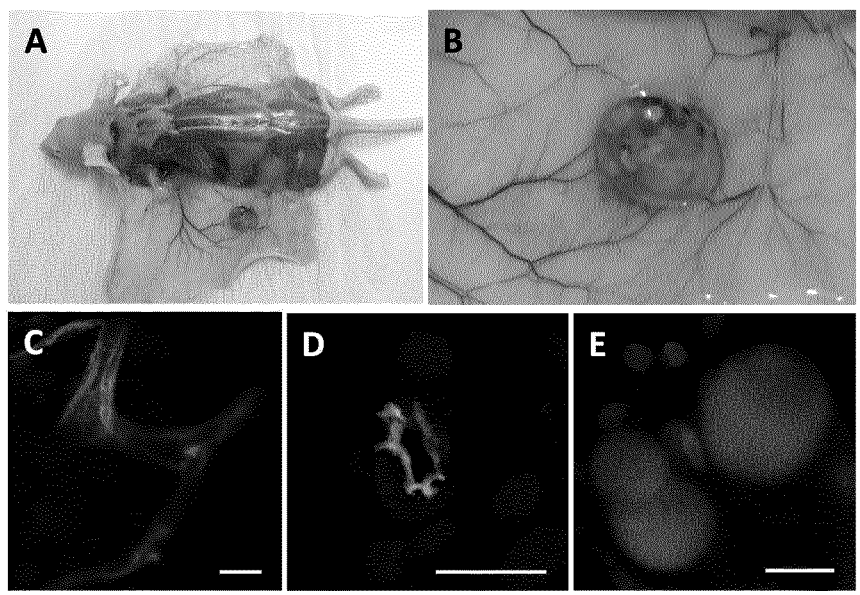
FIG. 9: Organoids become vascularized after transplantation. (A, B) Representative pictures of plugs containing spheroids 7 days after injection. (C,D) Hybrid blood vessels composed of human and mouse endothelial cells labeled with specific lectins. (E) Unilocular adipocytes in the explant are labeled with Bodipy and nuclei with DRAQS.

To test whether organoids can graft and are functional in vivo, the inventors transplanted spheroids subcutaneously in nude mice. They observed that the implant attracted blood vessels and became highly vascularized 7 days after transplantation (FIG. 9A, 9B). To demonstrate that the organoids were connected to the recipient circulatory system, they performed intravenous injection of distinct lectins that are specific to human or mouse vasculature. This showed that spheroids were perfused by a functional microvascular network, with the presence of chimeric human-mouse blood vessels (FIG. 9C, 9D). Moreover, large unilocular adipocytes were visible in the explant (FIG. 9E).

The invention claimed is:

1. An in vitro method of producing brown/beige adipocytes comprising:
   contacting cells selected from white adipose tissue cells and mesenchymal stem cells, with a differentiation medium comprising serum, a glucocorticoid and a mix of growth factors comprising a growth factor of the Vascular Endothelial Growth Factor (VEGF) family, a growth factor of the Epidermal Growth Factor (EGF) family, an insulin-like growth factor and a growth factor of the Fibroblast Growth Factor (FGF) family, until obtaining adipogenic progenitor cells,
   contacting said adipogenic progenitor cells with an adipogenic agent until obtaining brown/beige adipocytes, and
   optionally recovering said brown/beige adipocytes.

2. The method according to claim 1, wherein said cells are white adipose tissue cells or subcutaneous white adipose tissue cells.

3. The method according to claim 1, wherein the differentiation medium comprises:
   from about 0.1 ng/mL to about 20 ng/mL of a growth factor of the EGF family,
   from about 0.1 ng/mL to about 20 ng/mL a growth factor of the FGF family,
   from about 5 ng/mL to about 40 ng/mL of an insulin-like growth factor, and/or
   from about 0.05 ng/mL to about 5 ng/mL of a growth factor of the VEGF family.

4. The method according to claim 3, wherein the growth factor of the EGF family is EGF, the growth factor of the FGF family is FGF2, the insulin-like growth factor is IGF-1 or an analog thereof, and the growth factor of the VEGF family is VEGF.

5. The method according to claim 1, wherein the growth factor of the EGF family is EGF, the growth factor of the FGF family is FGF2, the insulin-like growth factor is IGF-1 or an analog thereof, and/or the growth factor of the VEGF family is VEGF.

6. The method according to claim 1, wherein said differentiation medium comprises from about 0.5% to about 10% serum, and/or from about 0.05 µg/mL to about 5 µg/mL of a glucocorticoid.

7. The method according to claim 1, wherein the serum is fetal bovine serum and the glucocorticoid is hydrocortisone.

8. The method according to claim 1, wherein said differentiation medium further comprises a free-radical scavenger or anti-oxidant.

9. The method according to claim 1, wherein said adipogenic agent is selected from the group consisting of insulin or analogs thereof, non-selective phosphodiesterase (PDE) inhibitors, beta-adrenergic agonists, thiazolidinediones, glucocorticoids, Bone Morphogenetic Proteins (BMPs), derivatives and mixtures thereof.

10. The method according to claim 9, wherein said adipogenic agent comprises one or more adipogenic agents selected from the group consisting of insulin, dexamethasone, indomethacin, IBMX, rosiglitazone, BMP4 and BMP7.

11. The method according to claim 1, wherein said adipogenic agent comprises a Bone Morphogenetic Protein and, optionally, insulin.

12. The method according to claim 1, wherein white adipose tissue cells or mesenchymal stem cells are contacted with the differentiation medium in a culture system enabling 3D spheroid formation, thereby producing spheroids of adipogenic progenitor cells.

13. The method according to claim 12, wherein spheroids of adipogenic progenitor cells are transferred into a 3D culture matrix mimicking the extracellular matrix and allowing three-dimensional growth, before to be contacted with the adipogenic agent.

14. The method according to claim 1, wherein said adipogenic agent comprises a Bone Morphogenetic Protein and, optionally, insulin and the growth factor of the EGF family is EGF, the growth factor of the FGF family is FGF2, the insulin-like growth factor is IGF-1 or an analog thereof, and the growth factor of the VEGF family is VEGF.

15. The method according to claim 1, wherein the glucocorticoid is hydrocortisone, the serum is fetal bovine serum and the mix of growth factors comprises VEGF-A, EGF, IGF-1 or an analog thereof, and FGF2.

16. The method according to claim 1, wherein the glucocorticoid is hydrocortisone, the serum is fetal bovine serum and the mix of growth factors comprises VEGF-A, EGF, IGF-1 or an analog thereof, and FGF2 and the adipogenic agent comprises a mixture of adipogenic agents and, optionally, insulin.

17. The method according to claim 16, wherein the mixture of adipogenic agents comprises one or several adipogenic agents selected from the group consisting of insulin, dexamethasone, indomethacin, IBMX, rosiglitazone, BMP4 and BMP7.

18. The method according to claim 1, wherein the differentiation medium consists essentially of fetal bovine serum, hydrocortisone, VEGF, EGF, IGF-1, insulin and FGF2.

19. The method according to claim 1, said method comprising:
contacting cells selected from white adipose tissue cells and mesenchymal stem cells, with a differentiation medium consisting essentially of fetal bovine serum, hydrocortisone and a mix of growth factors, said mix of growth factors consisting essentially of VEGF, EGF, FGF2, and IGF-1, until adipogenic progenitor cells are obtained;
replacing the differentiation medium with a replacement medium consisting essentially of one or more adipogenic agent and contacting said adipogenic progenitor cells with said replacement medium agent until brown/beige adipocytes are obtained, wherein the at least one adipogenic agent is BMP7, insulin, or a combination thereof; and
recovering said brown/beige adipocytes.

20. The method according to claim 19, wherein said replacement medium consists essentially of BMP7 and insulin.

* * * * *

UNITED STATES PATENT AND TRADEMARK OFFICE
CERTIFICATE OF CORRECTION

PATENT NO. : 12,065,673 B2
APPLICATION NO. : 15/743062
DATED : August 20, 2024
INVENTOR(S) : Frédéric Deschaseaux et al.

Page 1 of 1

It is certified that error appears in the above-identified patent and that said Letters Patent is hereby corrected as shown below:

In the Specification

Column 2,
Line 1, "MYFS" should read --MYF5--.
Line 4, "Net" should read --N et--.

Column 5,
Line 39, "PPARy" should read --PPARγ--.

Column 6,
Line 3, "PPARy2" should read --PPARγ2--.
Line 53, "DRAQS." should read --DRAQ5.--.

Column 8,
Line 49, "of means" should read --of" means--.

Column 9,
Line 65, "FGF-(3)." should read --FGF-β).--.

Column 15,
Line 18, "stored in 30 appropriate" should read --stored in appropriate--.

Column 21,
Line 29, "Pactin" should read --βactin--.

Column 25,
Line 53, "DRAQS" should read --DRAQ5--.

Signed and Sealed this
Twenty-first Day of October, 2025

John A. Squires
*Director of the United States Patent and Trademark Office*